(12) United States Patent
Flohr et al.

(10) Patent No.: US 7,414,049 B2
(45) Date of Patent: Aug. 19, 2008

(54) 4-OXO-2,3,4,5-TETRAHYDRO-BENZO[B][1,4] DIAZEPINE DERIVATIVES

(75) Inventors: Alexander Flohr, Reinach BL (CH); Roland Jakob-Roetne, Inzlingen (DE); Wolfgang Wostl, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/855,262

(22) Filed: Sep. 14, 2007

(65) Prior Publication Data

US 2008/0103133 A1 May 1, 2008

(30) Foreign Application Priority Data

Sep. 20, 2006 (EP) .................. 06120956

(51) Int. Cl.
*A61K 31/5513* (2006.01)
*C07D 243/12* (2006.01)

(52) U.S. Cl. ...................... 514/221; 540/517
(58) Field of Classification Search ............ 540/517; 514/221
See application file for complete search history.

(56) References Cited

U.S. PATENT DOCUMENTS 6,239,131 B1 5/2001 Shinozaki et al.

FOREIGN PATENT DOCUMENTS

| WO | WO 02/083652 A1 | 10/2002 |
| WO | WO 2004/069826 | 8/2004 |
| WO | WO 2005/023772 | 3/2005 |
| WO | WP 2005/040126 | 5/2005 |
| WO | WO06/061136 A2 | 6/2006 |

OTHER PUBLICATIONS

Sisodia, et al. Nature Reviews/Neuroscience, vol. 3, (Apr. 2002) pp. 281-290.
Beher et al., Biochemical Society Transactions (2002), vol. 30. part 4, pp. 534-537.
Wolfe, M., Current Topics in Medicinal Chemistry, 2002, 2, 371-383.
Tsai, et al., Current Medicinal Chemistry, 2002, vol. 9, No. 11, 1087-1106.
Sambamurti et al., Drug Development Research, 56, 211-227, 2002.
May, P., Drug Discovery Today, vol. 6, No. 9, May 2001, 459-462.
Nunan, et al., FEBS Letters, 483, (2000), 6-10.
Hardy, et al., Science, vol. 297, 353-356, Jul. 2002.
Wolfe, M., Journ. of Medicinal Chemistry, vol. 44, No. 13, 2001, 2039-2060.
Brockhaus et al., Neuroreport 9(7) 1481-1486 (1998).
Haass, C., The EMBO Journal (2004), 23, pp. 483-488.
Fraering, et al., Biochemistry (2004), 43 (30), pp. 9774-9789.
Herreman et al., Nature Cell Biology 2, 461-462, 2000.
De Stropper et al., Nature 398, 518-522, 1999.
Chung et al., Nature Cell Biology 3, 1129-1132, 2001.
Hadland et al., PNAS 98, 7487-7491, 2001.
Ferrando et al., Cancer Cell 1, 75-87, 2002.
Weng et al., Science 306, 269-271, 2004.
Weng et al., Mol Cell Biol 23, 655-664, 2003.
Weijzen et al., Nature Medicine 8, 979-986, 2002.
Nickoloff et al., Oncogene 22, 6598-6608, 2003.
Li et al., PNAS 97(11) 6138-6143, 2000.
Jacobs, et al, J. Med. Chem. 37, p. 1282 1994.
Szönyi et al., J. Fluorine Chemistry 55(1) p. 85, 1991.
Houston, Biochem. Pharmacol vol. 47, pp. 1469-1479, 1994.

*Primary Examiner*—Bruck Kifle
(74) *Attorney, Agent, or Firm*—George W. Johnston; Patricia S. Rocha-Tramaloni; Kimberly J. Prior

(57) ABSTRACT

The invention relates to 4-oxo-2,3,4,5-tetrahydro-benzo [b] [1,4]diazepines of formula I

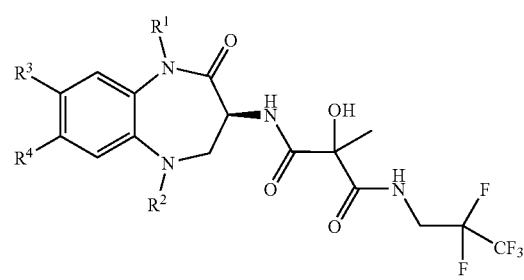

wherein $R^1$, $R^2$, $R^3$ and $R^4$ are as defined in the description and claims, which are γ-secretase inhibitors and which may be useful in the treatment of Alzheimer's disease.

8 Claims, No Drawings

4-OXO-2,3,4,5-TETRAHYDRO-BENZO[B][1,4] DIAZEPINE DERIVATIVES

PRIORITY TO RELATED APPLICATION(S)

This application claims the benefit of European Patent Application No. 06120956.5, filed Sep. 20, 2006, which is hereby incorporated by reference in its entirety.

BACKGROUND OF THE INVENTION

Alzheimer's disease (AD) is the most common cause of dementia in later life. Pathologically AD is characterized by the deposition in the brain of amyloid in extracellular plaques and intracellular neurofibrillary tangles. The amyloid plaques are mainly composed of amyloid peptides (Abeta peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Abeta peptides are derived from the same domain of the APP but differ at their N- and C-termini, the main species are of 40 and 42 amino-acid length. Abeta peptides are produced from APP through the sequential action of 2 proteolytic enzymes termed β- and γ-secretase. β-Secretase cleaves first in the extracellular domain of APP just outside of the trans-membrane domain (TM) to produce a C-terminal fragment of APP containing the TM- and cytoplasmatic domain (CTFβ). CTFβ is the substrate for γ-secretase which cleaves at several adjacent positions within the TM to produce the Aβ peptides and the cytoplasmic fragment. The majority of Abeta peptides is of 40 amino acids length (Aβ40), a minor species carries 2 additional amino acids at its C-terminus. Latter is supposed to be the more pathogenic amyloid peptide.

The β-secretase is a typical aspartyl protease. The γ-secretase is a proteolytic activity consisting of several proteins, its exact composition is incompletely understood. However, the presenilins are essential components of this activity and may represent a new group of atypical aspartyl proteases which cleave within the TM of their substrates and which are themselves polytopic membrane proteins. Other essential components of γ-secretase may be nicastrin and the products of the aph1 and pen-2 genes. Proven substrates for γ-secretase are the APP and the proteins of the Notch receptor family, however, γ-secretase has a loose substrate specificity and may cleave further membrane proteins unrelated to APP and Notch.

The γ-secretase activity is absolutely required for the production of Abeta peptides. This has been shown both by genetic means, i.e., ablation of the presenilin genes and by low-molecular-weight inhibitory compounds. Since according to the amyloid hypothesis or AD the production and deposition of Abeta is the ultimate cause for the disease, it is thought that selective and potent inhibitors of γ-secretase will be useful for the prevention and treatment of AD.

Numerous documents describe the current knowledge on γ-secretase inhibition, for example the following publications:
Nature Reviews/Neuroscience, Vol. 3, April 2002/281,
Biochemical Society Transactions (2002), Vol. 30. part 4,
Current Topics in Medicinal Chemistry, 2002, 2, 371-383,
Current Medicinal Chemistry, 2002, Vol. 9, No. 11, 1087-1106,
Drug Development Research, 56, 211-227, 2002,
Drug Discovery Today, Vol. 6, No. 9, May 2001, 459-462,
FEBS Letters, 483, (2000), 6-10,
Science, Vol. 297, 353-356, July 2002 and
Journal of Medicinal Chemistry, Vol. 44, No. 13, 2001, 2039-2060.

SUMMARY OF THE INVENTION

The invention provides 4-oxo-2,3,4,5-tetrahydro-benzo[b][1,4]diazepines of formula I

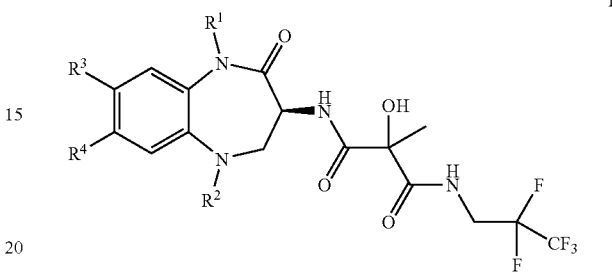

wherein
$R^1$ is hydrogen, lower alkyl substituted by halogen or lower alkyl substituted by hydroxy;
$R^2$ is lower alkyl substituted by halogen or lower alkyl substituted by hydroxy, or is $-COO(CH_2)_nR^5$;
n is 1, 2, or 3;
$R^5$ is hydroxy for n=2 or 3 or is lower alkyl substituted by halogen for n=1, 2 or 3; and
$R^3$ and $R^4$ are each independently hydrogen or halogen;

and pharmaceutically suitable acid addition salts, optically pure enantiomers, racemates and diastereomeric mixtures thereof.

The invention also provides all forms of optically pure enantiomers, racemates or diastereomeric mixtures for compounds of formula I.

The present invention further provides pharmaceutical compositions containing compounds of formula I per se, and methods of making compounds and compositions of the invention.

Compounds of formula I are γ-secretase inhibitors. Thus, the compounds of this invention will be useful treating Alzheimer's disease (AD) by blocking the activity of γ-secretase and reducing or preventing the formation of the various amyloidogenic Abeta peptides. The advantage of compounds of formula I for use in a drug is their good γ-secretase inhibition, together with their good thermodynamic solubility and/or bioavailability in comparison with compounds, disclosed in WO 2005/023772 and other related compounds.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred lower alkyl groups are groups with 1-4 carbon atoms.

The term "halogen" refers to chlorine, bromine, fluorine, or iodine.

The term "lower alkyl substituted by halogen" denotes an alkyl group as defined above, wherein at least one hydrogen atom is replaced by halogen, for example $CF_3$, $CHF_2$, $CH_2F$, $CH_2CF_3$, $CH_2CH_2F$, $CH_2CF_2CF_3$, $CH_2CH_2CF_2CF_3$ $CH_2CH_2CF_3$, $CH_2CH_2CH_2CF_3$ and the like. The term "lower alkyl substituted by hydroxy" denotes an alkyl group as defined above, wherein at least one hydrogen atom is replaced by a hydroxy group, for example, $CH_2CH_2OH$ or $CH_2CH_2CH_2OH$.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

The invention provides 4-oxo-2,3,4,5-tetrahydro-benzo[b][1,4]diazepines of formula I

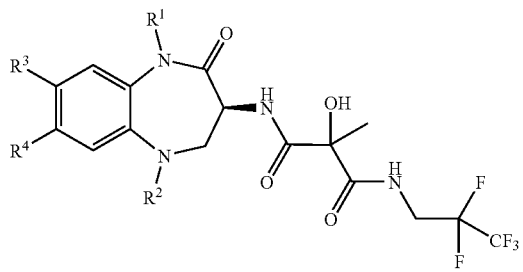

I wherein
$R^1$ is hydrogen, lower alkyl substituted by halogen or lower alkyl substituted by hydroxy,
$R^2$ is lower alkyl substituted by halogen or lower alkyl substituted by hydroxy, or is —$COO(CH_2)_nR^5$;
n is 1, 2, or 3;
$R^5$ is hydroxy for n=2 or 3 or is lower alkyl substituted by halogen for n=1, 2 or 3; and
$R^3$ and $R^4$ are each independently hydrogen or halogen;

and pharmaceutically suitable acid addition salts, optically pure enantiomers, racemates and diastereomeric mixtures thereof.

Preferred compounds of formula I are those, wherein $R^2$ is lower alkyl substituted by halogen, for example the following compounds:

N-[(S)-7-Fluoro-4-oxo-1-(2,2,2-trifluoro-ethyl)-2,3,4,5-tetrahydro-1H-benzo[b][1,4]diazepin-3-yl]-(R or S)-2-hydroxy-2-methyl-N'-(2,2,3,3,3-pentafluoro-propyl)-malonamide, (R or S)-2-Hydroxy-2-methyl-N-[(S)-4-oxo-1-(2,2,2-trifluoro-ethyl)-2,3,4,5-tetrahydro-1H-benzo[b][1,4]diazepin-3-yl]-N'-(2,2,3,3,3-pentafluoro-propyl)-malonamide, (S or R)-2-Hydroxy-2-methyl-N-[(S)-4-oxo-1-(3,3,3-trifluoro-propyl)-2,3,4,5-tetrahydro-1H-benzo[b][1,4]diazepin-3-yl]-N'-(2,2,3,3,3-pentafluoro-propyl)-malonamide, (R or S)-2-Hydroxy-2-methyl-N-[(S)-4-oxo-1-(4,4,4-trifluoro-butyl)-2,3,4,5-tetrahydro-1H-benzo[b][1,4]diazepin-3-yl]-N'-(2,2,3,3,3-pentafluoro-propyl)-malonamide, and (R or S)-2-Hydroxy-N-[(S)-1-(2-hydroxy-ethyl)-2-oxo-5-(2,2,2-trifluoro-ethyl)-2,3,4,5-tetrahydro-1H-benzo[b][1,4]diazepin-3-yl]-2-methyl-N'-(2,2,3,3,3-pentafluoro-propyl)-malonamide.

Further preferred compounds are those, wherein $R^2$ is lower alkyl substituted by hydroxy, for example the following compounds:

(RS)-2-Hydroxy-N-[(S)-1-(2-hydroxy-ethyl)-4-oxo-2,3,4,5-tetrahydro-1H-benzo[b][1,4]diazepin-3-yl]-2-methyl-N'-(2,2,3,3,3-pentafluoro-propyl)-malonamide and (R or S)-2-Hydroxy-N-[(S)-5-(2-hydroxy-ethyl)-2-oxo-1-(2,2,2-trifluoro-ethyl)-2,3,4,5-tetrahydro-1H-benzo[b][1,4]diazepin-3-yl]-2-methyl-N'-(2,2,3,3,3-pentafluoro-propyl)-malonamide.

Preferred compounds of formula I are further those, wherein $R^2$ is —$COO(CH_2)_nR^5$, n is 1, 2, or 3, and $R^5$ is hydroxy for n=2 or 3 or is lower alkyl substituted by halogen for n=1, 2 or 3, for example the following compounds:

(S)-7,8-Difluoro-3-[(R or S)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester, (S)-7,8-Difluoro-3-[(S or R)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester, (S)-7,8-Difluoro-3-[(R or S)-2-hydroxy-2-(2,2,3,3,3-pentafluoro-propylcarbamoyl)-propionylamino]-4-oxo-5-(2,2,2-trifluoro-ethyl)-2,3,4,5-tetrahydro-benzo[b][1,4]diazepine-1-carboxylic acid 2,2,2-trifluoro-ethyl ester, (S)-3-[(R or S)-2-Hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester, (S)-3-[(S or R)-2-Hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester, (S)-3-[(S or R)-2-Hydroxy-2-(2,2,3,3,3-pentafluoro-propylcarbamoyl)-propionylamino]-4-oxo-5-(2,2,2-trifluoro-ethyl)-2,3,4,5-tetrahydro-benzo[b][1,4]diazepine-1-carboxylic acid 2,2,2-trifluoro-ethyl ester, (S)-5-(2-Hydroxy-ethyl)-3-[(S or R)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester, (S)-3-[(S or R)-2-Hydroxy-2-(2,2,3,3,3-pentafluoro-propylcarbamoyl)-propionylamino]-4-oxo-5-(4,4,4-trifluoro-butyl)-2,3,4,5-tetrahydro-benzo[b][1,4]diazepine-1-carboxylic acid 4,4,4-trifluoro-butyl ester and (S)-5-(2-Hydroxy-ethyl)-3-[(S or R)-2-hydroxy-2-(2,2,3,3-pentafluoro-propylcarbamoyl)-propionylamino]-4-oxo-2,3,4,5-tetrahydro-benzo[b][1,4]diazepine-1-carboxylic acid 2-hydroxy-ethyl ester.

The present compounds of formula I and their pharmaceutically acceptable salts can be prepared by methods known in the art, for example, by processes described below, which processes comprise a) reacting a compound of formula

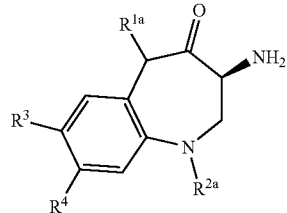

with a compound of formula

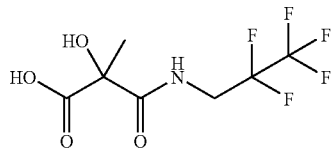

to produce a compound of formula

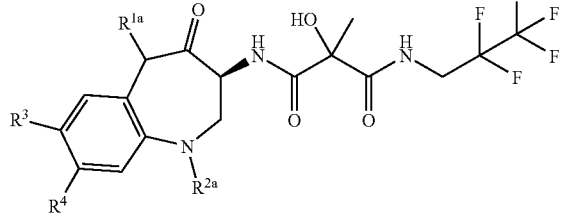

wherein $R^{1a}$, $R^{2a}$, $R^3$, and $R^4$ have the meaning as described above for $R^1$-$R^4$, except for the group —$CH_2$—$CH_2$—OH where $R^{1a}$ and $R^{2a}$ have the meaning of —$CH_2$—$CH_2$—OP, wherein P represents a hydroxy protecting group, and, if desired, converting the compounds obtained into pharmaceutically acceptable acid addition salts;

or b) reacting a compound of formula

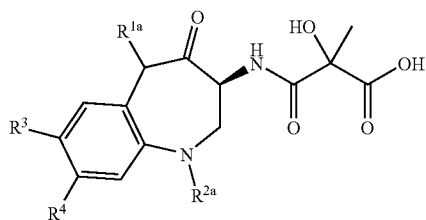

with a compound of formula

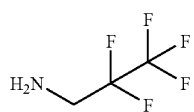

to produce a compound of formula

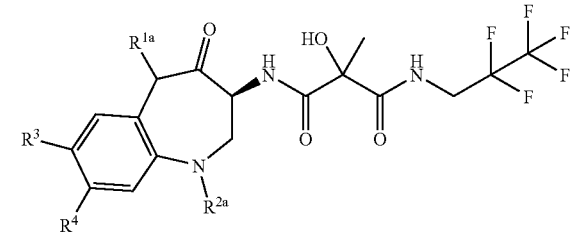

wherein $R^{1a}$, $R^{2a}$, $R^3$, and $R^4$ have the meaning as described above for $R^1$-$R^4$, except for the group —$CH_2$—$CH_2$—OH where $R^{1a}$ and $R^{2a}$ have the meaning of —$CH_2$—$CH_2$—OP, wherein P represents a hydroxy protecting group, and, if desired, converting the compounds obtained into pharmaceutically acceptable acid addition salts;

or c) cleaving the hydroxy protecting group(s) of a compound of formula

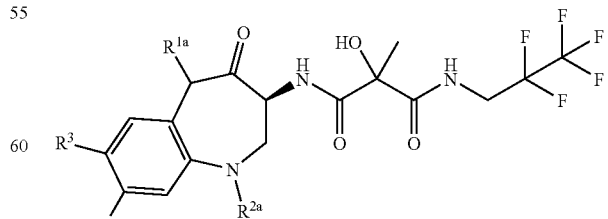

to produce a compound of formula

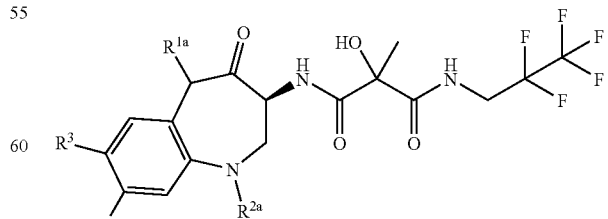

wherein $R^1$, $R^2$, $R^3$, and $R^4$ have the meaning as described above and, if desired, converting the compounds obtained into pharmaceutically acceptable acid addition salts.

The detailed description can be found below and in Examples 1-14. The starting material of formula IV is a known compound and the amine of formula V is a commercial available product.

The starting compounds of formula IIa and II to manufacture compounds of formula I and Ia may be prepared as follows:

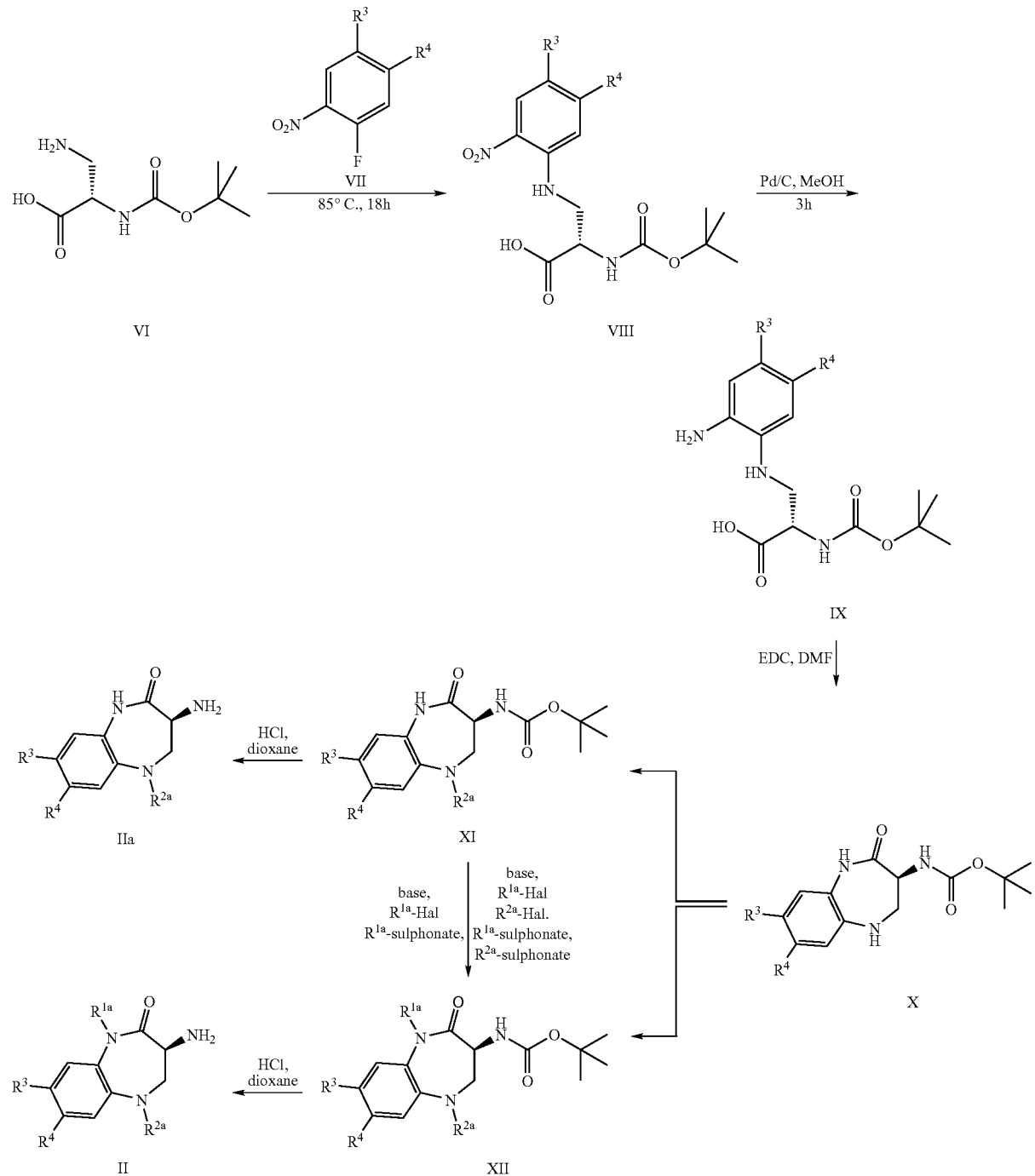

Scheme 1

In analogy to the procedure described in U.S. Pat. No. 6,239,131, compounds of formula VIII can be prepared by treatment of N-protected 2,3-diamino-propionic acids, e.g. (S)-3-amino-2-tert-butoxycarbonylamino-propionic acid with 1,4-difluoro-2-nitrobenzene or 1,2,4-trifluoro-5-nitro-benzene. A compound of formula VIII is obtained which is then hydrogenated with Pd on carbon (10%) to yield a compound of formula IX.

The compound of formula IX is then treated with a condensating agent, e.g. with N-(3-dimethylaminopropyl)-N'-ethyl-carbodiimide hydrochloride to yield the cyclised compound of formula X.

The introduction of substituents $R^{1a}$ and $R^{2a}$ in compounds of formula X can be carried out in a manner known per se by using an alkylating agent, e.g. halogenide, methanesulphonate, trifluoromethanesulphonate, or 4-toluonesulphonate in combination with a base, e.g. sodium hydrogencarbonate, cesium carbonate, sodium hydride, or lithium bis(trimethylsilyl)amide to obtain compounds of formula XI and XII.

When $R^2$ or $R^{2a}$ has the meaning of a carbamate, the carbamoylation of compounds of formula X can be achieved by using an alkylating agent, e.g. halogenide, methanesulphonate, trifluoromethanesulphonate, or 4-toluonesulphonate in combination with a base, e.g. sodium hydrogencarbonate, cesium carbonate, sodium hydride, or lithium bis(trimethylsilyl)amide and in presence of carbondioxide to obtain the corresponding compounds of formula XI and XII.

A compound of formula IIa or II may be obtained by treating compounds of formula XI or XII with acid, preferably with trifluoroacetic acid in dichloromethane or with aqueous hydrochloric acid.

Compounds of formula I can be manufactured in accordance with the invention, wherein, $R^1$, $R^2$, $R^{10}$, $R^{2a}$, $R^3$, $R^4$ and n are as described above, as follows (scheme 2):

To a solution of a compound of formula II or IIa in tetrahydrofurane is added the compound of formula III, 1-hydroxybenzotriazole hydrate, N-(3-dimethylaminpropyl)-N'-ethyl-carbodiimide hydrochloride and N-ethyldiisopropylamine. After stirring at room temperature over night the solvent is removed by distillation and the residue is purified to obtain compounds of formula Ia.

Compounds of formula Ia in which hydroxy groups are present in protected form can be transformed to compounds of formula I by cleaving off the protecting group(s). Examples of hydroxy protecting groups are ether protecting groups such as tetrahydropyranyl, allyl, trityl, tert-butyldim-ethylsilyl, preferably benzyl. The cleavage of hydroxy protecting groups which may be present can be carried out in a manner known per se, e.g. by acidic hydrolysis, by means of Lewis acids, or in the case of the preferred benzyl group, by hydrogenolysis.

Scheme 2

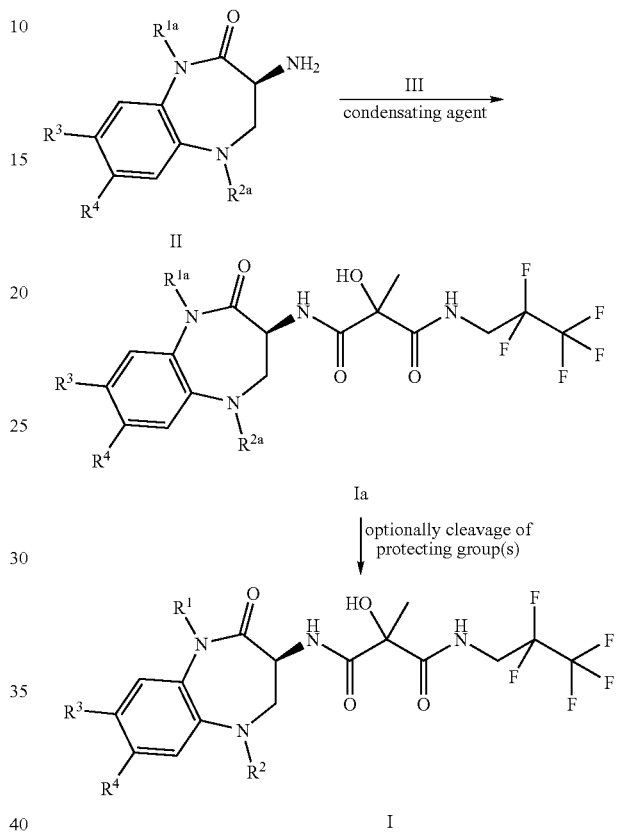

An alternative process for the preparation of compounds of formula I can be followed in accordance with scheme 3, wherein, $R^1$, $R^2$, $R^{1a}$, $R^{2a}$, $R^3$, $R^4$ and n are as described above.

Scheme 3

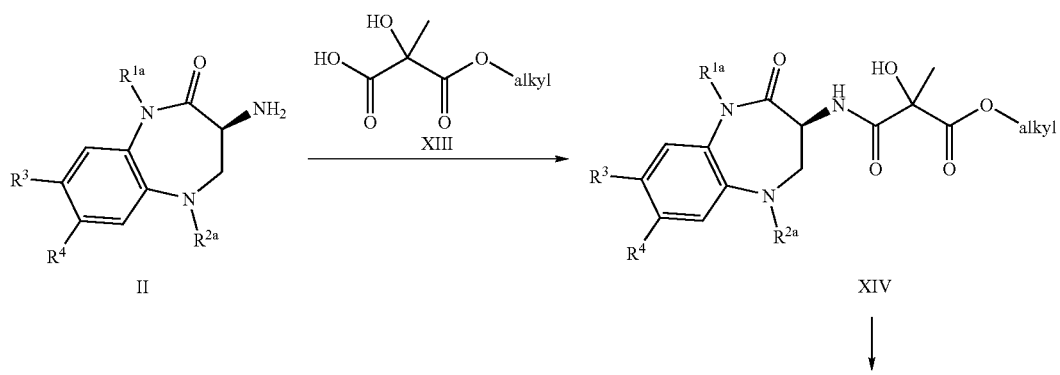

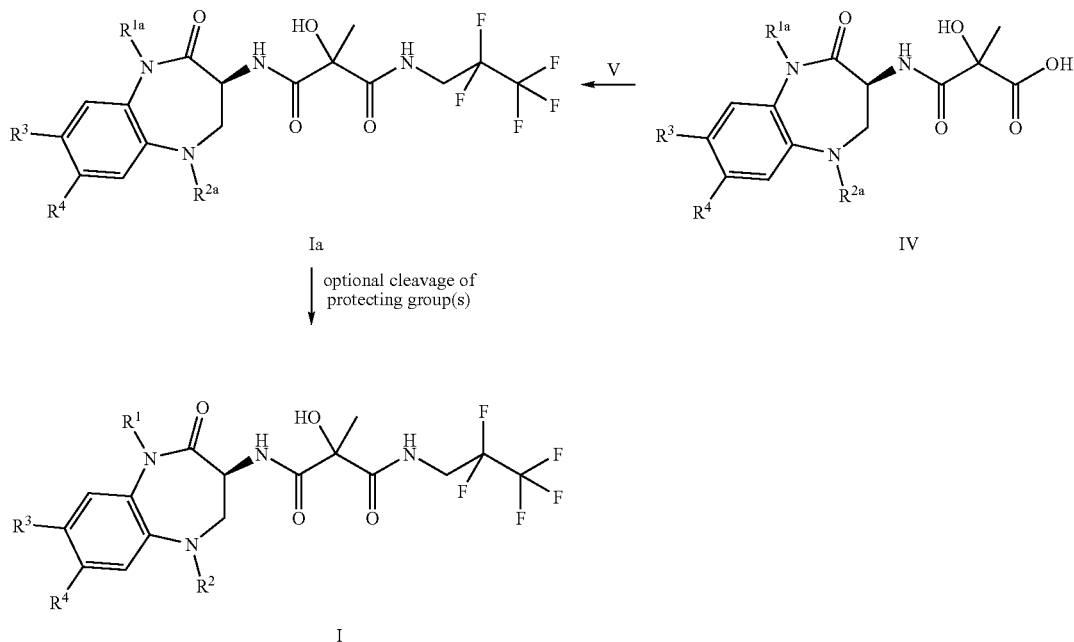

Ia optional cleavage of protecting group(s)

I

A compound of formula I can be obtained as follows:

To a solution of a compound of formula II or IIa in tetrahydrofurane is added a compound of formula XIII, for example 2-hydroxy-2-methyl-malonic acid monomethyl ester, 1-hydroxybenzotriazole hydrate, N-(3-dimethylaminopropyl)-N'-ethyl-carbodiimide hydrochloride and N-ethyldiisopropylamine. After stirring at room temperature over night the solvent is removed by distillation, and the residue is purified to obtain compounds of formula XIV. Saponification of the ester function in compounds of formula XIV, preferably using basic conditions, yields the carboxylic acid of formula IV, which in turn is treated with 2,2,3,3,3-pentafluoro-propylamine (V) under the condensating conditions already described above to give compounds of formula Ia or I respectively.

Compounds of formula Ia in which hydroxy groups are present in protected form can be transformed to compounds of formula I by cleaving off the protecting group(s). Examples of hydroxy protecting groups are ether protecting groups such as tetrahydropyranyl, allyl, trityl, tert-butyldimethylsilyl, preferably benzyl. The cleavage of hydroxy protecting groups which may be present can be carried out in a manner known per se, e.g. by acidic hydrolysis, by means of Lewis acids, or in the case of the preferred benzyl group, by hydrogenolysis.

The acid addition salts of compounds of formula I can be converted to the corresponding free bases by treatment with at least a stoichiometric equivalent of a suitable base such as sodium or potassium hydroxide, potassium carbonate, sodium bicarbonate, ammonia, and the like. Compounds of I and Ia can also exist in optically pure form. Separation into antipodes can be effected according to methods known per se either at an early stage of the synthesis or, preferably, at a later stage by separation of the diastereomeric products by chromatography, optionally on chiral phases.

EXAMPLE 1

(S)-7,8-Difluoro-3-[(R or S)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester and (S)-7,8-Difluoro-3-[(S or R)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester

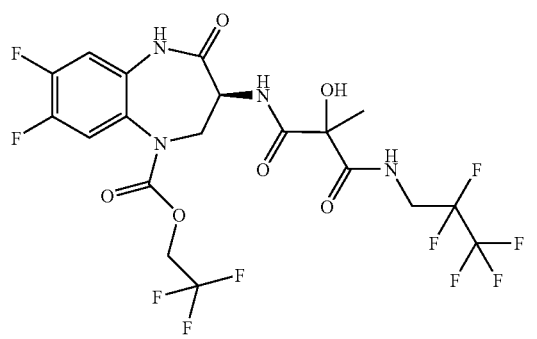

I a) (S)-3-(2-Amino-4,5-difluoro-phenylamino)-2-tert-butoxycarbonylamino-propionic acid and 3-(4-Amino-2,5-difluoro-phenylamino)-2-tert-butoxycarbonylamino-propionic acid

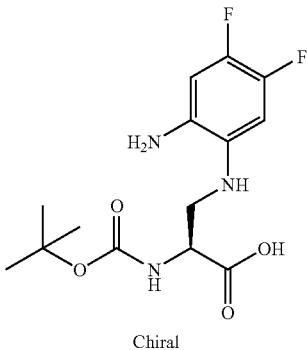

Chiral

A dispersion of 6.0 g (28.8 mmol) of (S)-3-amino-2-tert-butoxycarbonylamino-propionic acid in 190 ml of ethanol was treated with 5.2 g (28.8 mmol) of 2,4,5-trifluoronitrobenzene and 4.0 g (28.8 mmol) of potassium carbonate. The reaction mixture was heated to 85° C. under stirring for 18 hours. For the working-up, the orange coloured solution was completely evaporated, the residue distributed between water (250 ml) and ethyl acetate (250 ml), and, thereupon, the aqueous layer re-extracted with ethyl acetate (2×250 ml). The combined organic layers were washed with water (2×100 ml). The aqueous layers were combined and the pH adjusted to 4.4. Thereafter, the aqueous layer was extracted with ethyl acetate (5×250 ml), then the organic layers combined, dried over sodium sulphate, and evaporated under reduced pressure. The mixture of (S)-2-tert-butoxycarbonylamino-3-(4,5-difluoro-2-nitro-phenylamino)-propionic acid and (S)-2-tert-butoxycarbonylamino-3-(2,5-difluoro-4-nitro-phenylamino)-propionic acid, 8.8 g of a yellow solid, was engaged in the next step without further purification.

The thus obtained mixture was dissolved in 250 ml of methanol, and 0.52 g of palladium on carbon (10%) were added thereto. The resultant mixture was stirred for 3 hours under a hydrogen atmosphere under ambient pressure. For the working-up, the mixture was filtrated, and the filtrate was evaporated under reduced pressure. There were obtained 7.97 g of a mixture of (S)-3-(2-amino-4,5-difluoro-phenylamino)-2-tert-butoxycarbonylamino-propionic acid and 3-(4-amino-2,5-difluoro-phenylamino)-2-tert-butoxycarbonylamino-propionic acid as a dark foam which was engaged in the next step without further purification.

b) (S)-7,8-Difluoro-2-oxo-2,3,4,5-tetrahydro-1H-benzo[b][1,4]diazepin-3-yl)-carbamic acid tert-butyl ester

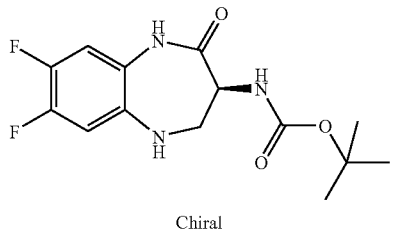

Chiral

A solution of 7.97 g of a mixture of (S)-3-(2-amino-4,5-difluoro-phenylamino)-2-tert-butoxycarbonylamino-propionic acid and 3-(4-amino-2,5-difluoro-phenylamino)-2-tert-butoxycarbonylamino-propionic acid in 90 ml of N,N-dimethylformamide was treated consecutively with 10.2 g (77 mmol) of N-ethyldiisopropylamine, 3.6 g (26.5 mmol) of 1-hydroxy-benzotriazole and 5.2 g (26.5 mmol) of N-(3-dimethylaminpropyl)-N'-ethyl-carbodiimide hydrochloride under stirring at 0° C. Stirring was continued for 18 hours while the reaction mixture was left to warm to room temperature. For the working-up, the reaction mixture was evaporated under reduced pressure, thereafter, the residue was treated with water, and the aqueous phase extracted with ethyl acetate (2×400 ml). The combined organic layers were dried over sodium sulphate and evaporated under reduced pressure. For purification, the dark solid obtained was separated on silica gel using a gradient of heptane/ethyl acetate=100/0 to 50/50 as the eluent.

There were obtained 1.4 g (18% of theory) of ((S)-7,8-difluoro-2-oxo-2,3,4,5-tetrahydro-1H-benzo[b][1,4]diazepin-3-yl)-carbamic acid tert-butyl ester as a light yellow solid; MS (m/e) 314 (M+H)$^+$.

c) (S)-3-tert-Butoxycarbonylamino-7,8-difluoro-4-oxo-2,3,4,5-tetrahydro-benzo[b][1,4]diazepine-1-carboxylic acid 2,2,2-trifluoro-ethyl ester

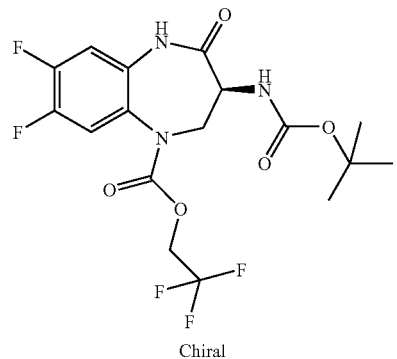

Chiral

A solution of 200 mg of (S)-7,8-difluoro-2-oxo-2,3,4,5-tetrahydro-1H-benzo[b][1,4]diazepin-3-yl)-carbamic acid tert-butyl ester in 6 ml of N,N-dimethylformamide was treated with 312 mg of cesium carbonate, 229 mg of 2,2,2-trifluoroethyl trifluoromethanesulphonate, and about 200 mg of solid carbondioxide. The reaction mixture was stirred in a sealed tube at room temperature for 4 hours. For the working-up, the solvent was evaporated under reduced pressure, and the residue was distributed between 10 ml of a saturated sodium hydrogencarbonate solution and 30 ml of ethyl acetate. The aqueous layer was separated and extracted twice with 30 ml of ethyl acetate. The combined organic layers were dried over sodium sulphate and evaporated under reduced pressure. For purification, the light yellow foam was separated on silica gel using a gradient of heptane/ethyl acetate=100/0 to 50/50 as the eluent. There were obtained 130 mg (46% of theory) of the title compound [MS (m/e): 440 (M+H)$^+$] and 127 mg of (S)-3-tert-butoxycarbonylamino-7,8-difluoro-4-oxo-5-(2,2,2-trifluoro-ethyl)-2,3,4,5-tetrahydro-benzo[b][1,4]diazepine-1-carboxylic acid 2,2,2-trifluoro-ethyl ester MS (m/e): 522 (M+H)$^+$] as the by-product.

d) (S)-3-Amino-7,8-difluoro-4-oxo-2,3,4,5-tetrahydro-benzo[b][1,4]diazepine-1-carboxylic acid 2,2,2-trifluoro-ethyl ester hydrochloride

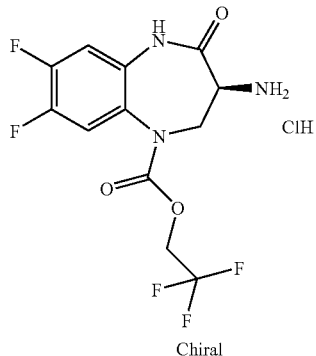

A solution of 120 mg of (S)-3-tert-butoxycarbonylamino-7,8-difluoro-4-oxo-5-(2,2,2-trifluoro-ethyl)-2,3,4,5-tetrahydro-benzo[b][1,4]diazepine-1-carboxylic acid 2,2,2-trifluoro-ethyl ester in 4 ml of dioxane was treated with 0.27 ml of hydrochlorid acid (37%). The reaction mixture was warmed to 50° C. for 3 hours. For the working-up, the mixture was evaporated under reduced pressure. The oily residue was evaporated three times with 25 ml of toluene to yield thereby quantitatively the title compound as a light yellow solid which was engaged in the next step without further purification; MS (m/e): 340 (M+H)$^+$.

e) (S)-7,8-Difluoro-3-[(R or S)-2-hydroxy-2-(2,2,3,3, 3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester and (S)-7, 8-Difluoro-3-[(S or R)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester A solution of 103 mg of (S)-3-amino-7,8-difluoro-4-oxo-2,3,4,5-tetrahydro-benzo[b][1,4]diazepine-1-carboxylic acid 2,2,2-trifluoro-ethyl ester hydrochloride in 6 ml of tetrahydrofurane was treated consecutively with 80 mg of (RS)-2-hydroxy-2-methyl-N-(2,2,3,3,3-pentafluoro-propyl)-malonamic acid, 0.15 ml of N-ethyldiisopropylamine, 42 mg of 1-hydroxy-benzotriazole, and 59 mg of N-(3-dimethylaminpropyl)-N'-ethyl-carbodiimide hydrochloride under stirring at 0° C. Stirring was continued for 18 hours while the reaction mixture was left to warm to room temperature. For the working-up, the reaction mixture was evaporated under reduced pressure and the residue was directly separated on silica gel using a gradient of heptane/ethyl acetate=100/0 to 50/50 as the eluent. There were obtained 65 mg (41% of theory) of a 1:1-mixture of the epimeric title compounds as a white foam; MS (m/e): 587 (M+H)$^+$.

The two epimers were partly separated by HPLC on a chiral phase (Chiralpak AD) using a 4:1-mixture of heptane and ethanol as the eluent yielding the first eluting epimer (−)-(S)-7,8-difluoro-3-[(R or S)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester as a brownish solid [MS (m/e): 587 (M+H)$^+$] and a 3:7-mixture of (+)-(−)-(S)-7,8-difluoro-3-[(S and R)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester as a brownish solid; MS (m/e): 587 (M+H)$^+$.

EXAMPLE 2

(S)-7,8-Difluoro-3-[(R or S)-2-hydroxy-2-(2,2,3,3,3-pentafluoro-propylcarbamoyl)-propionylamino]-4-oxo-5-(2,2,2-trifluoro-ethyl)-2,3,4,5-tetrahydro-benzo[b][1,4]diazepine-1-carboxylic acid 2,2,2-trifluoro-ethyl ester and (S)-7,8-difluoro-3-[(S or R)-2-hydroxy-2-(2,2,3,3,3-pentafluoro-propylcarbamoyl)-propionylamino]-4-oxo-5-(2,2,2-trifluoro-ethyl)-2,3,4,5-tetrahydro-benzo[b][1,4]diazepine-1-carboxylic acid 2,2,2-trifluoro-ethyl ester

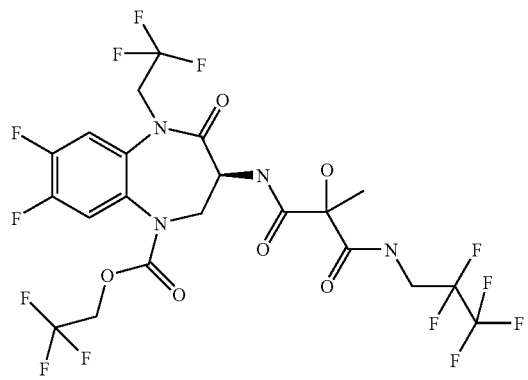

a) [(S)-7,8-Difluoro-2-oxo-1-(2,2,2-trifluoro-ethyl)-2,3,4,5-tetrahydro-1H-benzo[b][1,4]diazepin-3-yl]-carbamic acid tert-butyl ester

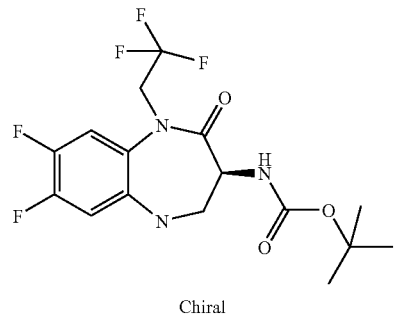

A solution of 200 mg of ((S)-7,8-difluoro-2-oxo-2,3,4,5-tetrahydro-1H-benzo[b][1,4]diazepin-3-yl)-carbamic acid tert-butyl ester in 7 ml of tetrahydrofurane was cooled to −78° C. under an argon atmosphere. Thereafter, the solution was treated with 0.62 ml of lithium bis(trimethylsilyl)amide (1 M solution in tetrahydrofurane), stirred for 30 min at −78° C., then warmed to room temperature before 0.13 ml of 2,2,2-trifluoroethyl trifluoromethanesulphonate were added to the reaction mixture. After stirring overnight in a sealed flask, another 0.05 ml of 2,2,2-trifluoroethyl trifluoromethanesulphonate were added and stirring continued for 18 hours. For the working-up, the reaction mixture was evaporated under reduced pressure and the residue was directly submitted to chromatography on a Si—NH$_2$ phase using a gradient of heptane/ethyl acetate=100/0 to 60/30 as the eluent. There were obtained 193 mg (77% of theory) of the title compound as a white foam; MS 418 (M+Na)$^+$.

b) (S)-3-tert-butoxycarbonylamino-7,8-difluoro-4-oxo-5-(2,2,2-trifluoro-ethyl)-2,3,5-tetrahydro-benzo[b][1,4]diazepine-1-carboxylic acid 2,2,2-trifluoro-ethyl ester

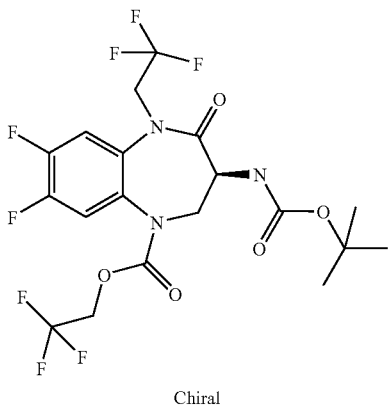

Chiral

In an analogous procedure to that described in Example 1c), the [(S)-7,8-difluoro-2-oxo-1-(2,2,2-trifluoro-ethyl)-2,3,4,5-tetrahydro-1H-benzo[b][1,4]diazepin-3-yl]-carbamic acid tert-butyl ester was treated with cesium carbonate, solid carbondioxide, and trifluoroethyl trifluoromethanesulphonate at 60° C. for 18 hours in a sealed flask to yield the title compound (83% of theory) as a white foam; MS (m/e): 522 (M+H)$^+$.

c) (S)-3-Amino-7,8-difluoro-4-oxo-5-(2,2,2-trifluoro-ethyl)-2,3,4,5-tetrahydro-benzo[b][1,4]diazepine-1-carboxylic acid 2,2,2-trifluoro-ethyl ester hydrochloride

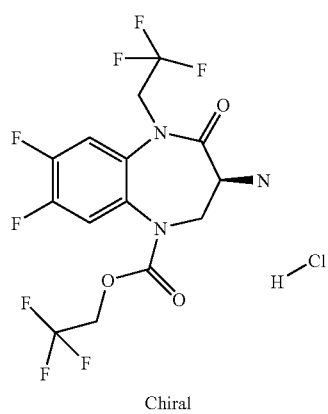

Chiral

In an analogous procedure to that described in Example 1d), the treatment of the (S)-3-tert-butoxycarbonylamino-7,8-difluoro-4-oxo-5-(2,2,2-trifluoro-ethyl)-2,3,4,5-tetrahydro-benzo[b][1,4]diazepine-1-carboxylic acid 2,2,2-trifluoro-ethyl with hydrochlorid acid (37%) in dioxane yielded the title compound as a light yellow foam; MS (m/e): 422 (M+H)$^+$].

d) (S)-7,8-Difluoro-3-[(R or S)-2-hydroxy-2-(2,2,3,3,3-pentafluoro-propylcarbamoyl) -propionylamino]-4-oxo-5-(2,2,2-trifluoro-ethyl)-2,3,4,5-tetrahydro-benzo[b][1,4]diazepine-1-carboxylic acid 2,2,2-trifluoro-ethyl ester and (S)-7,8-difluoro-3-[(S or R)-2-hydroxy-2-(2,2,3,3,3-pentafluoro-propylcarbamoyl)-propionylamino]-4-oxo-5-(2,2,2-trifluoro-ethyl)-2,3,4,5-tetrahydro-benzo[b][1,4]diazepine-1-carboxylic acid 2,2,2-trifluoro-ethyl ester In an analogous procedure to that described in Example 1e) the condensation of (S)-3-amino-7,8-difluoro-4-oxo-5-(2,2,2-trifluoro-ethyl)-2,3,4,5-tetrahydro-benzo[b][1,4]diazepine-1-carboxylic acid 2,2,2-trifluoro-ethyl ester hydrochloride and (RS)-2-hydroxy-2-methyl-N-(2,2,3,3,3-pentafluoro-propyl)-malonamic acid with 1-hydroxy-benzotriazole and N-(3-dimethylaminpropyl)-N'-ethyl-carbodiimide hydrochloride as the condensating agents yielded a 1:1-mixture of the epimeric title compounds as a white foam; MS (m/e): 669 (M+H)$^+$. The two epimers were separated by HPLC on a chiral phase (Chiralpak AD) using a 4:1-mixture of heptane and isopropanol as the eluent yielding the first eluting epimer (−)-(S)-7,8-difluoro-3-[(R or S)-2-hydroxy-2-(2,2,3,3,3-pentafluoro-propylcarbamoyl)-propionylamino]-4-oxo-5-(2,2,2-trifluoro-ethyl)-2,3,4,5-tetrahydro-benzo[b][1,4]diazepine-1-carboxylic acid 2,2,2-trifluoro-ethyl ester as a light yellow solid [MS (m/e): 669 (M+H)$^+$] and the second eluting epimer (−)-(S)-7,8-difluoro-3-[(S or R)-2-hydroxy-2-(2,2,3,3,3-pentafluoro-propylcarbamoyl)-propionylamino]-4-oxo-5-(2,2,2-trifluoro-ethyl)-2,3,4,5-tetrahydro-benzo[b][1,4]diazepine-1-carboxylic acid 2,2,2-trifluoro-ethyl ester as a light yellow foam; MS (m/e): 669 (M+H)$^+$.

EXAMPLE 3

N-[(S)-7-Fluoro-4-oxo-1-(2,2,2-trifluoro-ethyl)-2,3,4,5-tetrahydro-1H-benzo[b][1,4]diazepin-3-yl]-(R or S)-2-hydroxy-2-methyl-N'-(2,2,3,3,3-pentafluoro-propyl)-malonamide and N-[(S)-7-Fluoro-4-oxo-1-(2,2,2-trifluoro-ethyl)-2,3,4,5-tetrahydro-1H-benzo[b][1,4]diazepin-3-yl]-(S or R)-2-hydroxy-2-methyl-N'-(2,2,3,3,3-pentafluoro-propyl)-malonamide

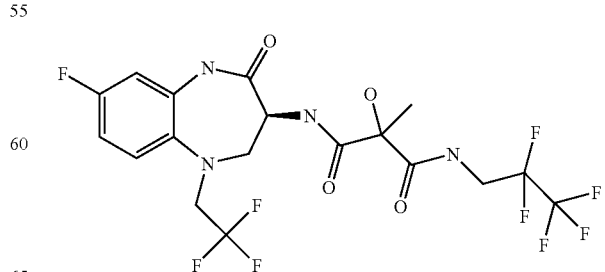

a) (S)-8-Fluoro-2-oxo-2,3,4,5-tetrahydro-1H-benzo[b][1,4]diazepin-3-yl)-carbamic acid tert-butyl ester

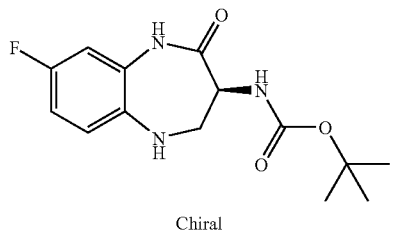

Chiral

In analogy to the procedure described in Example 1b), the intramolecular condensation of (S)-3-(2-amino-4-fluoro-phenylamino)-2-tert-butoxycarbonylamino-propionic acid with N-ethyldiisopropylamine, 1-hydroxy-benzotriazole, and N-(3-dimethylaminpropyl)-N'-ethyl-carbodiimide hydrochloride yielded the title compound as a yellow solid; MS (m/e): 296 (M+H)$^+$.

(S)-3-(2-amino-4-fluoro-phenylamino)-2-tert-butoxycarbonylamino-propionic acid was obtained in analogy to the procedure described in U.S. Pat. No. 6,239,131.

b) [(S)-7-Fluoro-4-oxo-1-(2,2,2-trifluoro-ethyl)-2,3,4,5-tetrahydro-1H-benzo[b][1,4]diazepin-3-yl]-carbamic acid tert-butyl ester

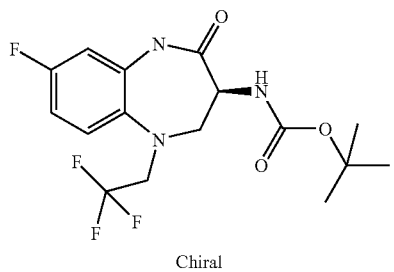

Chiral

A mixture of 2.1 g of (S)-8-fluoro-2-oxo-2,3,4,5-tetrahydro-1H-benzo[b][1,4]diazepin-3-yl)-carbamic acid tert-butyl ester, 3.0 g of sodium hydrogencarbonate, and 8.5 g of 2,2,2-trifluoroethyl trifluoromethanesulphonate in 10 ml of N,N-dimethylformamide was heated at 60° C. for 6 days in a sealed flask. For the working-up, the reaction mixture was evaporated under reduced pressure and the residue dissolved in 100 ml of saturated sodium hydrogencarbonate solution and 100 ml of ethyl acetate. The aqueous layer was extracted twice with 100 ml of ethyl acetate. The combined organic layers were dried over sodium sulphate, then evaporated under reduced pressure. For purification, the light brown oil was separated on silica gel using a gradient of heptane/ethyl acetate=100/0 to 60/30 as the eluent. There were obtained 0.86 g (32% of theory) of the title compound as a white foam; MS (m/e): 378 (M+H)$^+$.

c) (S)-3-Amino-8-fluoro-5-(2,2,2-trifluoro-ethyl)-1,3,4,5-tetrahydro-benzo[b][1,4]diazepin-2-one hydrochloride

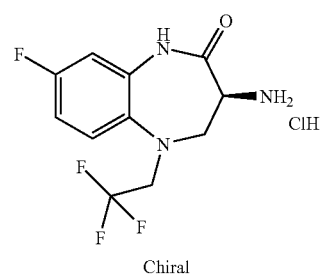

Chiral

In an analogous procedure to that described in Example 1d), the treatment of the [(S)-7-fluoro-4-oxo-1-(2,2,2-trifluoro-ethyl)-2,3,4,5-tetrahydro-1H-benzo[b][1,4]diazepin-3-yl]-carbamic acid tert-butyl ester with hydrochlorid acid (37%) in dioxane yielded the title compound as a light brown foam; MS (m/e): 278 (M+H)$^+$.

d) N-[(S)-7-Fluoro-4-oxo-1-(2,2,2-trifluoro-ethyl)-2,3,4,5-tetrahydro-1H-benzo[b][1,4]diazepin-3-yl]-(R or S)-2-hydroxy-2-methyl-N'-(2,2,3,3,3-pentafluoro-propyl)-malonamide and N-[(S)-7-Fluoro-4-oxo-1-(2,2,2-trifluoro-ethyl)-2,3,4,5-tetrahydro-1H-benzo[b][1,4]diazepin-3-yl]-(S or R)-2-hydroxy-2-methyl-N'-(2,2,3,3,3-pentafluoro-propyl)-malonamide In an analogous procedure to that described in Example 1e), the condensation of (S)-3-amino-8-fluoro-5-(2,2,2-trifluoro-ethyl)-1,3,4,5-tetrahydro-benzo[b][1,4]diazepin-2-one hydrochloride and (RS)-2-hydroxy-2-methyl-N-(2,2,3,3,3-pentafluoro-propyl)-malonamic acid with 1-hydroxy-benzotriazole and N-(3-dimethylaminpropyl)-N'-ethyl-carbodiimide hydrochloride as the condensating agents yielded a 1:1-mixture of the epimeric title compounds as a white foam; MS (m/e): 525 (M+H)$^+$.

The two epimers were separated by HPLC on a chiral phase (Chiralpak AD) using a 4:1-mixture of heptane and ethanol as the eluent yielding the first eluting epimer N-[(S)-7-fluoro-4-oxo-1-(2,2,2-trifluoro-ethyl)-2,3,4,5-tetrahydro-1H-benzo[b][1,4]diazepin-3-yl]-(R or S)-2-hydroxy-2-methyl-N'-(2,2,3,3,3-pentafluoro-propyl)-malonamide as a white foam [MS (m/e): 525 (M+H)$^+$] and the second eluting epimer N-[(S)-7-fluoro-4-oxo-1-(2,2,2-trifluoro-ethyl)-2,3,4,5-tetrahydro-1H-benzo[b][1,4]diazepin-3-yl]-(S or R)-2-hydroxy-2-methyl-N'-(2,2,3,3,3-pentafluoro-propyl)-malonamide as a white foam [MS (m/e): 525 (M+H)$^+$].

EXAMPLE 4

(R or S)-2-Hydroxy-2-methyl-N-[(S)-4-oxo-1-(2,2,2-trifluoro-ethyl)-2,3,4,5-tetrahydro-1H-benzo[b][1,4]diazepin-3-yl]-N'-(2,2,3,3,3-pentafluoro-propyl)-malonamide and (S or R)-2-Hydroxy-2-methyl-N-[(S)-4-oxo-1-(2,2,2-trifluoro-ethyl)-2,3,4,5-tetrahydro-1H-benzo[b][1,4]diazepin-3-yl]-N'-(2,2,3,3,3-pentafluoro-propyl)-malonamide

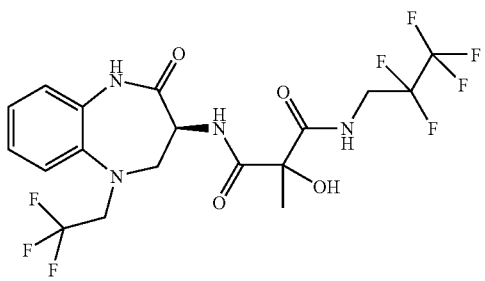

a) [(S)-4-Oxo-1-(2,2,2-trifluoro-ethyl)-2,3,4,5-tetrahydro-1H-benzo[b][1,4]diazepin-3-yl]-carbamic acid tert-butyl ester

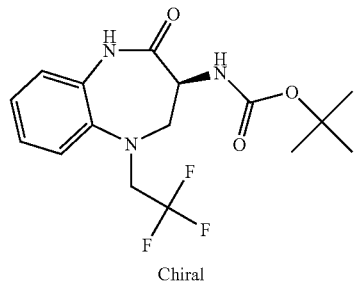

Chiral

In an analogous procedure to that described in Example 3b), the (S)-2-oxo-2,3,4,5-tetrahydro-1H-benzo[b][1,4]diazepin-3-yl)-carbamic acid tert-butyl ester was treated with 2,2,2-trifluoroethyl trifluoromethanesulphonate in presence of sodium hydrogencarbonate in N,N-dimethylformamide at 60° C. for 4 days in a sealed flask. After separation of mainly unchanged starting material by chromatography on silica gel using a gradient of heptane/ethyl acetate=100/0 to 60/30 as the eluent, the title compound was obtained as a white solid in 22% of theory, MS (m/e): 360 (M+H)$^+$.

b) (S)-3-Amino-5-(2,2,2-trifluoro-ethyl)-1,3,4,5-tetrahydro-benzo[b][1,4]diazepin-2-one Hydrochloride

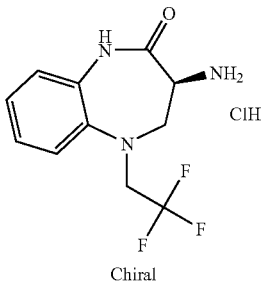

Chiral

In an analogous procedure to that described in Example 1d), the treatment of the [(S)-4-oxo-1-(2,2,2-trifluoro-ethyl)-2,3,4,5-tetrahydro-1H-benzo[b][1,4]diazepin-3-yl]-carbamic acid tert-butyl ester with hydrochlorid acid (37%) in dioxane yielded the title compound as a light yellow solid; MS (m/e): 260 (M+H)$^+$.

c) (R or S)-2-Hydroxy-2-methyl-N-[(S)-4-oxo-1-(2,2,2-trifluoro-ethyl)-2,3,4,5-tetrahydro-1H-benzo[b][1,4]diazepin-3-yl]-N'-(2,2,3,3,3-pentafluoro-propyl)-malonamide and (S and R)-2-Hydroxy-2-methyl-N-[(S)-4-oxo-1-(2,2,2-trifluoro-ethyl)-2,3,4,5-tetrahydro-1H-benzo[b][1,4]diazepin-3-yl]-N'-(2,2,3,3,3-pentafluoro-propyl)-malonamide In an analogous procedure to that described in Example 1e), the condensation of (S)-3-amino-5-(2,2,2-trifluoro-ethyl)-1,3,4,5-tetrahydro-benzo[b][1,4]diazepin-2-one hydrochloride and (RS)-2-hydroxy-2-methyl-N-(2,2,3,3,3-pentafluoro-propyl)-malonamic acid with 1-hydroxy-benzotriazole and N-(3-dimethylaminpropyl)-N'-ethyl-carbodiimide hydrochloride as the condensating agents yielded a 1:1-mixture of the epimeric title compounds as a white foam; MS (m/e): 507 (M+H)$^+$.

The two epimers were separated by HPLC on a chiral phase (Chiralpak AD) using a 4:1-mixture of heptane and isopropanol as the eluent yielding the first eluting epimer (R or S)-2-hydroxy-2-methyl-N-[(S)-4-oxo-1-(2,2,2-trifluoro-ethyl)-2,3,4,5-tetrahydro-1H-benzo[b][1,4]diazepin-3-yl]-N'-(2,2,3,3,3-pentafluoro-propyl)-malonamide as a light yellow solid [MS (m/e): 507 (M+H)$^+$] and the second eluting epimer (S or R)-2-hydroxy-2-methyl-N-[(S)-4-oxo-1-(2,2,2-trifluoro-ethyl)-2,3,4,5-tetrahydro-1H-benzo[b][1,4]diazepin-3-yl]-N'-(2,2,3,3,3-pentafluoro-propyl)-malonamide as a light yellow solid [MS (m/e): 507 (M+H)$^+$].

EXAMPLE 5

(R or S)-2-Hydroxy-2-methyl-N-[(S)-4-oxo-1-(3,3,3-trifluoro-propyl)-2,3,4,5-tetrahydro-1H-benzo[b][1,4]diazepin-3-yl]-N'-(2,2,3,3,3-pentafluoro-propyl)-malonamide and (S or R)-2-Hydroxy-2-methyl-N-[(S)-4-oxo-1-(3,3,3-trifluoro-propyl)-2,3,4,5-tetrahydro-1H-benzo[b][1,4]diazepin-3-yl]-N'-(2,2,3,3,3-pentafluoro-propyl)-malonamide

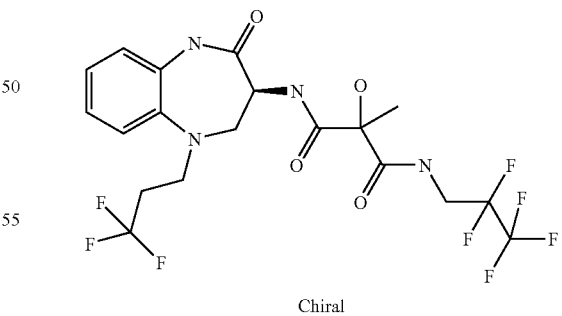

Chiral a) [(S)-4-Oxo-1-(3,3,3-trifluoro-propyl)-2,3,4,5-tetrahydro-1H-benzo[b][1,4]diazepin-3-yl]-carbamic acid tert-butyl ester In an analogous procedure to that described in Example 3b), the (S)-2-oxo-2,3,4,5-tetrahydro-1H-benzo[b][1,4]diaz epin-3-yl)-carbamic acid tert-butyl ester was treated with 1,1,1-trifluoro-3-iodpropane and lithium iodide in presence of sodium hydrogencarbonate in N,N-dimethylformamide at 60° C. for 10 days in a sealed flask. After separation of mainly unchanged starting material by chromatography on silica gel using a gradient of heptane/ethyl acetate=100/0 to 60/30 as the eluent, the title compound was obtained as a white foam [yield 26% of theory; MS (m/e): 374 (M+H)$^+$].

b) (S)-3-Amino-5-(3,3,3-trifluoro-propyl)-1,3,4,5-tetrahydro-benzo[b][1,4]diazepin-2-one: Hydrochloride

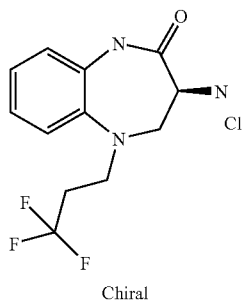

In an analogous procedure to that described in Example 1d), the treatment of the [(S)-4-oxo-1-(3,3,3-trifluoro-propyl)-2,3,4,5-tetrahydro-1H-benzo[b][1,4]diazepin-3-yl]-carbamic acid tert-butyl ester with hydrochlorid acid (37%) in dioxane yielded the title compound as an off-white solid; MS (m/e): 274 (M+H)$^+$.

c) (R or S)-2-Hydroxy-2-methyl-N-[(S)-4-oxo-1-(3,3,3-trifluoro-propyl)-2,3,4,5-tetrahydro-1H-benzo[b][1,4]diazepin-3-yl]-N'-(2,2,3,3,3-pentafluoro-propyl)-malonamide and (S or R)-2-Hydroxy-2-methyl-N-[(S)-4-oxo-1-(3,3,3-trifluoro-propyl)-2,3,4,5-tetrahydro-1H-benzo[b][1,4]diazepin-3-yl]-N'-(2,2,3,3,3-pentafluoro-propyl)-malonamide In an analogous procedure to that described in Example 1e), the condensation of (S)-3-amino-5-(3,3,3-trifluoro-propyl)-1,3,4,5-tetrahydro-benzo[b][1,4]diazepin-2-one hydrochloride and (RS)-2-hydroxy-2-methyl-N-(2,2,3,3,3-pentafluoro-propyl)-malonamic acid with 1-hydroxybenzotriazole and N-(3-dimethylaminpropyl)-N'-ethylcarbodiimide hydrochloride as the condensating agents yielded a 1:1-mixture of the epimeric title compounds as a white foam; MS (m/e): 521 (M+H)$^+$.

The two epimers were separated on silica gel using a gradient of heptane and ethyl acetate 100/0 to 50/50 as the eluent yielding the first eluting epimer (R or S)-2-hydroxy-2-methyl-N-[(S)-4-oxo-1-(3,3,3-trifluoro-propyl)-2,3,4,5-tetrahydro-1H-benzo[b][1,4]diazepin-3-yl]-N'-(2,2,3,3,3-pentafluoro-propyl)-malonamide [MS (m/e): 521 (M+H)$^+$] and the second eluting epimer (S or R)-2-hydroxy-2-methyl-N-[(S)-4-oxo-1-(3,3,3-trifluoro-propyl)-2,3,4,5-tetrahydro-1H-benzo[b][1,4]diazepin-3-yl]-N'-(2,2,3,3,3-pentafluoro-propyl)-malonamide [MS (m/e): 507 (M+H)$^+$], both as a white foam.

EXAMPLE 6

(R or S)-2-Hydroxy-2-methyl-N-[(S)-4-oxo-1-(4,4,4-trifluoro-butyl)-2,3,4,5-tetrahydro-1H-benzo[b][1,4]diazepin-3-yl]-N'-(2,2,3,3,3-pentafluoro-propyl)-malonamide and (S or R)-2-Hydroxy-2-methyl-N-[(S)-4-oxo-1-(4,4,4-trifluoro-butyl)-2,3,4,5-tetrahydro-1H-benzo[b][1,4]diazepin-3-yl]-N'-(2,2,3,3,3-pentafluoro-propyl)-malonamide

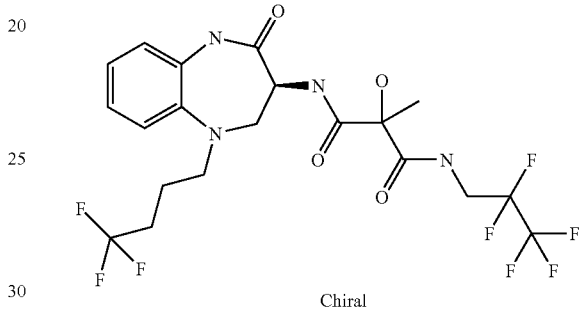

a) [(S)-4-Oxo-1-(4,4,4-trifluoro-butyl)-2,3,4,5-tetrahydro-1H-benzo[b][1,4]diazepin-3-yl]-carbamic acid tert-butyl ester

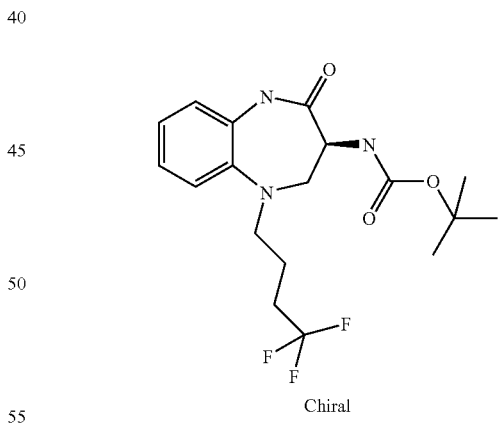

In an analogous procedure to that described in Example 3b), the (S)-2-oxo-2,3,4,5-tetrahydro-1H-benzo[b][1,4]diazepin-3-yl)-carbamic acid tert-butyl ester was treated with 4-bromo-1,1,1-trifluoro-butane and lithium iodide in presence of sodium hydrogencarbonate in N,N-dimethylformamide at 60° C. for the weekend in a sealed flask. After chromatography on silica gel using a gradient of heptane/ethyl acetate=100/0 to 60/30 as the eluent, the title compound was obtained as a white foam [yield 84% of theory, MS (m/e): 388 (M+H)$^+$].

b) (S)-3-Amino-5-(4,4,4-trifluoro-butyl)-1,3,4,5-tetrahydro-benzo[b][1,4]diazepin-2-one Hydrochloride

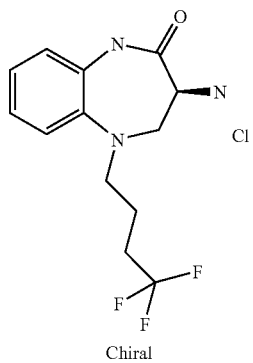

Chiral

In an analogous procedure to that described in Example 1d), the treatment of the [(S)-4-oxo-1-(4,4,4-trifluoro-butyl)-2,3,4,5-tetrahydro-1H-benzo[b][1,4]diazepin-3-yl]-carbamic acid tert-butyl ester with hydrochlorid acid (37%) in dioxane yielded the title compound as a light yellow solid; MS (m/e): 288 (M+H)$^+$.

c) (R or S)-2-Hydroxy-2-methyl-N-[(S)-4-oxo-1-(4,4,4-trifluoro-butyl)-2,3,4,5-tetrahydro-1H-benzo[b][1,4]diazepin-3-yl]-N'-(2,2,3,3,3-pentafluoro-propyl)-malonamide and (S or R)-2-Hydroxy-2-methyl-N-[(S)-4-oxo-1-(4,4,4-trifluoro-butyl)-2,3,4,5-tetrahydro-1H-benzo[b][1,4]diazepin-3-yl]-N'-(2,2,3,3,3-pentafluoro-propyl)-malonamide In an analogous procedure to that described in Example 1e), the condensation of (S)-3-amino-5-(4,4,4-trifluoro-butyl)-1,3,4,5-tetrahydro-benzo[b][1,4]diazepin-2-one hydrochloride and (RS)-2-hydroxy-2-methyl-N-(2,2,3,3,3-pentafluoro-propyl)-malonamic acid with 1-hydroxybenzotriazole and N-(3-dimethylaminpropyl)-N'-ethyl-carbodiimide hydrochloride as the condensating agents yielded a 1:1-mixture of the epimeric title compounds as an off-white foam; MS (m/e): 535 (M+H)$^+$.

The two epimers were separated by HPLC on a chiral phase (Chiralpak AD) using a 4:1-mixture of heptane and ethanol as the eluent yielding the first eluting epimer (R or S)-2-hydroxy-2-methyl-N-[(S)-4-oxo-1-(4,4,4-trifluoro-butyl)-2,3,4,5-tetrahydro-1H-benzo[b][1,4]diazepin-3-yl]-N'-(2,2,3,3,3-pentafluoro-propyl)-malonamide as a light yellow foam [MS (m/e): 535 (M+H)$^+$] and the second eluting epimer (S or R)-2-hydroxy-2-methyl-N-[(S)-4-oxo-1-(4,4,4-trifluoro-butyl)-2,3,4,5-tetrahydro-1H-benzo[b][1,4]diazepin-3-yl]-N'-(2,2,3,3,3-pentafluoro-propyl)-malonamide as a light yellow solid [MS (m/e): 535 (M+H)$^+$].

EXAMPLE 7

(RS)-2-Hydroxy-N-[(S)-1-(2-hydroxy-ethyl)-4-oxo-2,3,4,5-tetrahydro-1H-benzo[b][1,4]diazepin-3-yl]-2-methyl-N'-(2,2,3,3,3-pentafluoro-propyl)-malonamide

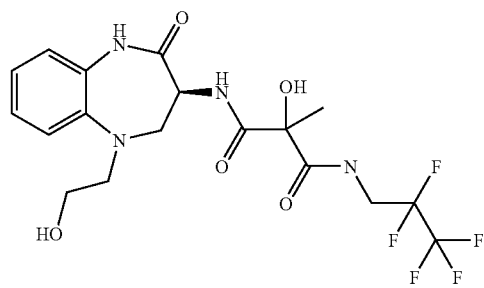

a) [(S)-1-(2-Benzyloxy-ethyl)-4-oxo-2,3,4,5-tetrahydro-1H-benzo[b][1,4]diazepin-3-yl]-carbamic acid tert-butyl ester

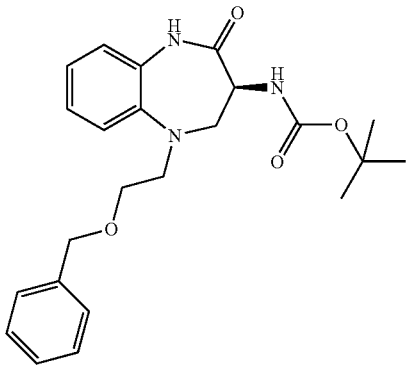

Chiral

A mixture of 500 mg of (S)-2-oxo-2,3,4,5-tetrahydro-1H-benzo[b][1,4]diazepin-3-yl)-carbamic acid tert-butyl ester, 303 mg of sodium hydrogencarbonate, 271 mg of lithium iodide, and 0.59 ml of benzyl 2-bromoethylether in 0.5 ml of N,N-dimethylformamide was stirred at 60° C. in a sealed tube during the weekend. For the working-up, the reaction mixture was treated with 20 ml of saturated sodium hydrogencarbonate solution and with 40 ml of ethyl acetate. The aqueous layer was separated and extracted twice with 40 ml of ethyl acetate. The combined organic layers were dried over sodium sulphate and, thereafter, evaporated under reduced pressure. After separation of unchanged starting material by chromatography on silica gel using a gradient of heptane/ethyl acetate=100/0 to 60/40 as the eluent, 223 mg (30% of theory) of the title compound were obtained as a white foam; MS (m/e): 412 (M+H)$^+$.

b) (S)-3-Amino-5-(2-benzyloxy-ethyl)-1,3,4,5-tetrahydro-benzo[b][1,4]diazepin-2-one Hydrochloride

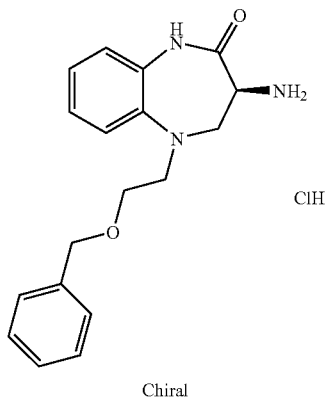

Chiral

In an analogous manner to that described in Example 1d), the treatment of the [(S)-1-(2-benzyloxy-ethyl)-4-oxo-2,3,4,5-tetrahydro-1H-benzo[b][1,4]diazepin-3-yl]-carbamic acid tert-butyl ester with hydrochlorid acid (37%) in dioxane yielded the title compound as a light yellow foam; MS (m/e): 312 (M+H)$^+$.

c) N-[(S)-1-(2-Benzyloxy-ethyl)-4-oxo-2,3,4,5-tetrahydro-1H-benzo[b][1,4]diazepin-3-yl]-2-hydroxy-2-methyl-N'-(2,2,3,3,3-pentafluoro-propyl)-malonamide

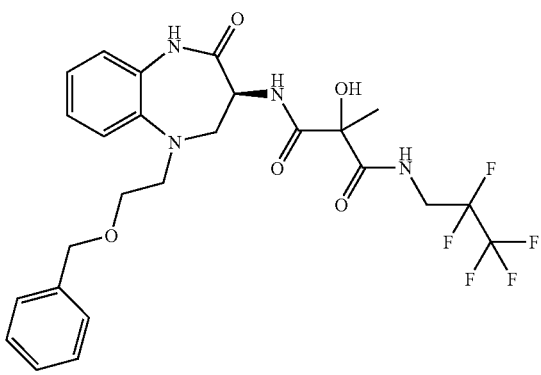

In an analogous manner to that described in Example 1e), the condensation of (S)-3-amino-5-(2-benzyloxy-ethyl)-1,3,4,5-tetrahydro-benzo[b][1,4]diazepin-2-one hydrochloride and (RS)-2-hydroxy-2-methyl-N-(2,2,3,3,3-pentafluoropropyl)-malonamic acid with 1-hydroxy-benzotriazole and N-(3-dimethylaminpropyl)-N'-ethyl-carbodiimide hydrochloride as the condensating agents yielded a 1:1-mixture of the epimeric title compounds as a light yellow solid; MS (m/e) 559 (M+H)$^+$.

d) (RS)-2-Hydroxy-N-[(S)-1-(2-hydroxy-ethyl)-4-oxo-2,3,4,5-tetrahydro-1H-benzo[b][1,4]diazepin-3-yl]-2-methyl-N'-(2,2,3,3,3-pentafluoro-propyl)-malonamide A solution of 26 mg of N-[(S)-1-(2-benzyloxy-ethyl)-4-oxo-2,3,4,5-tetrahydro-1H-benzo[b][1,4]diazepin-3-yl]-2-hydroxy-2-methyl-N'-(2,2,3,3,3-pentafluoro-propyl)-malonamide in 2.0 ml of methanol was treated with 10 mg of palladium on carbon (10%) and stirred for 3 days under an atmosphere of hydrogen. During this period of time, the catalyst was replaced three times after filtration of the reaction mixture over Dicalit. For the final working-up, the reaction mixture was filtrated over Dicalit and the solvent evaporated under reduced pressure. After separation of mainly unchanged starting material by chromatography on silica gel using a gradient of heptane/ethyl acetate=100/0 to 20/80 as the eluent, 6 mg (29% of theory) of the title compound were obtained as a white foam; MS (m/e): 469 (M+H)$^+$.

EXAMPLE 8

(R or S)-2-Hydroxy-N-[(S)-5-(2-hydroxy-ethyl)-2-oxo-1-(2,2,2-trifluoro-ethyl)-2,3,4,5-tetrahydro-1H-benzo[b][1,4]diazepin-3-yl]-2-methyl-N'-(2,2,3,3,3-pentafluoro-propyl)-malonamide

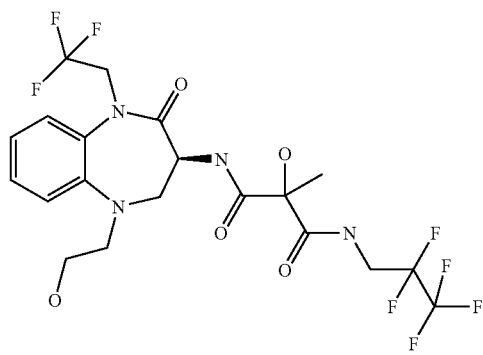

Chiral a) [(S)-5-(2-Benzyloxy-ethyl)-2-oxo-1-(2,2,2-trifluoro-ethyl)-2,3,4,5-tetrahydro-1H-benzo[b][1,4]diazepin-3-yl]-carbamic acid tert-butyl ester

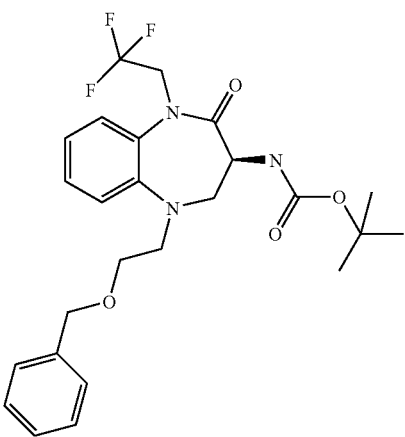

Chiral

In an analogous manner to that described in Example 2a), the alkylation of the [(S)-1-(2-benzyloxy-ethyl)-4-oxo-2,3,4,5-tetrahydro-1H-benzo[b][1,4]diazepin-3-yl]-carbamic acid tert-butyl ester with 2,2,2-trifluoroethyl trifluoromethane-sulphonate using lithium bis(trimethylsilyl)amide (1M solution in tetrahydrofurane) as the base yielded title compound as a white foam (yield 86% of theory); MS (m/e): 494 (M+H)⁺.

b) (S)-3-Amino-5-(2-benzyloxy-ethyl)-1-(2,2,2-trifluoro-ethyl)-1,3,4,5-tetrahydro-benzo[b][1,4]diazepin-2-one Hydrochloride

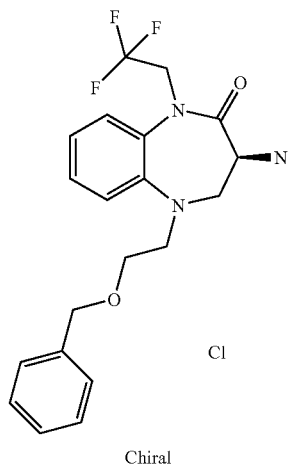

Chiral

In an analogous manner to that described in Example 1d), the treatment of the [(S)-5-(2-benzyloxy-ethyl)-2-oxo-1-(2,2,2-trifluoro-ethyl)-2,3,4,5-tetrahydro-1H-benzo[b][1,4]diazepin-3-yl]-carbamic acid tert-butyl ester with hydrochlorid acid (37%) in dioxane yielded the title compound as a light yellow foam; MS (m/e): 394 (M+H)⁺.

c) (R or S)-N-[(S)-5-(2-Benzyloxy-ethyl)-2-oxo-1-(2,2,2-trifluoro-ethyl)-2,3,4,5-tetrahydro-1H-benzo[b][1,4]diazepin-3-yl]-2-hydroxy-2-methyl-N'-(2,2,3,3,3-pentafluoro-propyl)-malonamide and (S or R)-N-[(S)-5-(2-Benzyloxy-ethyl)-2-oxo-1-(2,2,2-trifluoro-ethyl)-2,3,4,5-tetrahydro-1H-benzo[b][1,4]diazepin-3-yl]-2-hydroxy-2-methyl-N'-(2,2,3,3,3-pentafluoro-propyl)-malonamide

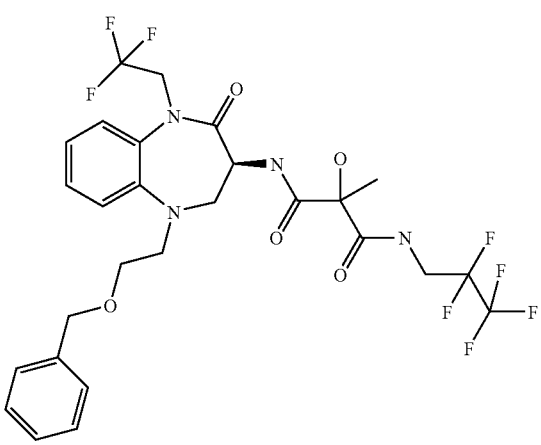

In an analogous manner to that described in Example 1e), the condensation of (S)-3-amino-5-(2-benzyloxy-ethyl)-1-(2,2,2-trifluoro-ethyl)-1,3,4,5-tetrahydro-benzo[b][1,4]diazepin-2-one hydrochloride and (RS)-2-hydroxy-2-methyl-N-(2,2,3,3,3-pentafluoro-propyl)-malonamic acid with 1-hydroxy-benzotriazole and N-(3-dimethylaminpropyl)-N'-ethyl-carbodiimide hydrochloride as the condensating agents yielded a 1:1-mixture of the epimeric title compounds as a white foam; MS (m/e): 641 (M+H)⁺.

The two epimers were separated by HPLC on a chiral phase (Chiralpak AD) using a 85:15-mixture of heptane and isopropanol as the eluent yielding the first eluting epimer (R or S) -N-[(S)-5-(2-benzyloxy-ethyl)-2-oxo-1-(2,2,2-trifluoro-ethyl)-2,3,4,5-tetrahydro-1H-benzo[b][1,4]diazepin-3-yl]-2-hydroxy-2-methyl-N'-(2,2,3,3,3-pentafluoro-propyl)-malonamide as a light yellow viscous oil [MS (m/e): 639 (M−H)⁻] and the second eluting epimer (S or R)-N-[(S)-5-(2-benzyloxy-ethyl)-2-oxo-1-(2,2,2-trifluoro-ethyl)-2,3,4,5-tetrahydro-1H-benzo[b][1,4]diazepin-3-yl]-2-hydroxy-2-methyl-N'-(2,2,3,3,3-pentafluoro-propyl)-malonamide as a light yellow foam [MS (m/e): 639 (M−H)⁻].

d) (R or S)-2-Hydroxy-N-[(S)-5-(2-hydroxy-ethyl)-2-oxo-1-(2,2,2-trifluoro-ethyl)-2,3,4,5-tetrahydro-1H-benzo[b][1,4]diazepin-3-yl]-2-methyl-N'-(2,2,3,3,3-pentafluoro-propyl)-malonamide A solution of 72 mg of the first eluting epimer (R or S)-N-[(S)-5-(2-benzyloxy-ethyl)-2-oxo-1-(2,2,2-trifluoro-ethyl)-2,3,4,5-tetrahydro-1H-benzo[b][1,4]diazepin-3-yl]-2-hydroxy-2-methyl-N'-(2,2,3,3,3-pentafluoro-propyl)-malonamide in 3.0 ml of methanol was treated with 24 mg of palladium on carbon (10%) and stirred for 24 hours under an atmosphere of hydrogen. For the working-up, the reaction mixture was filtrated over Dicalit and the solvent evaporated under reduced pressure. The crude material was purified by chromatography on silica gel using a gradient of heptane/ethyl acetate=100/0 to 30/60 as the eluent, and 46 mg (79% of theory) of the title compound were obtained as a white foam; MS (m/e): 551 (M+H)⁺.

EXAMPLE 9

(R or S)-2-Hydroxy-N-[(S)-1-(2-hydroxy-ethyl)-2-oxo-5-(2,2,2-trifluoro-ethyl)-2,3,4,5-tetrahydro-1H-benzo[b][1,4]diazepin-3-yl]-2-methyl-N'-(2,2,3,3,3-pentafluoro-propyl)-malonamide

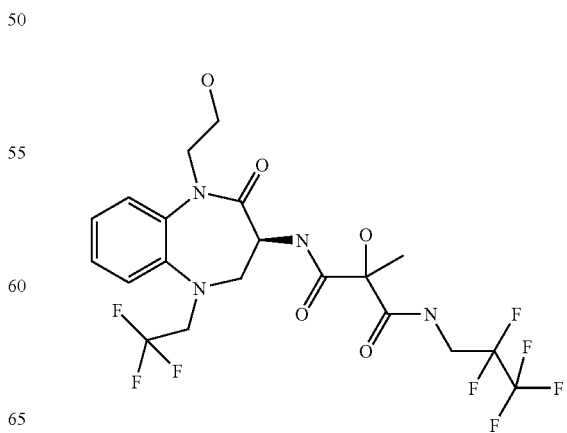

a) [1-(2-Benzyloxy-ethyl)-2-oxo-5-(2,2,2-trifluoro-ethyl)-2,3,4,5-tetrahydro-1H-benzo[b][1,4]diazepin-3-yl]-carbamic acid tert-butyl ester

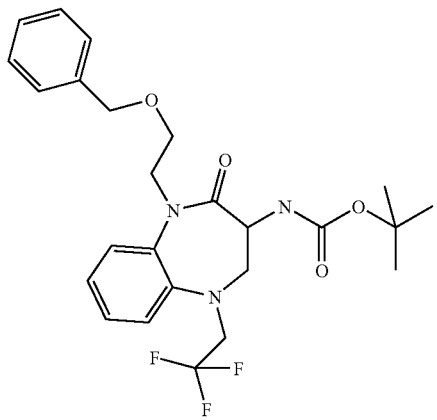

In an analogous manner to that described in Example 2a), the alkylation of the [(S)-4-oxo-1-(2,2,2-trifluoro-ethyl)-2,3,4,5-tetrahydro-1H-benzo[b][1,4]diazepin-3-yl]-carbamic acid tert-butyl ester [Example 4a)] with benzyl 2-bromoethylether in presence of lithium iodide and using lithium bis(trimethylsilyl)amide (1M solution in tetrahydrofurane) as the base yielded the isomerised title compound (55.4:44.6) as a colourless viscous oil (yield 75% of theory); MS (m/e): 494 (M+H)$^+$.

b) 3-Amino-1-(2-benzyloxy-ethyl)-5-(2,2,2-trifluoro-ethyl)-1,3,4,5-tetrahydro-benzo[b][1,4]diazepin-2-one Hydrochloride

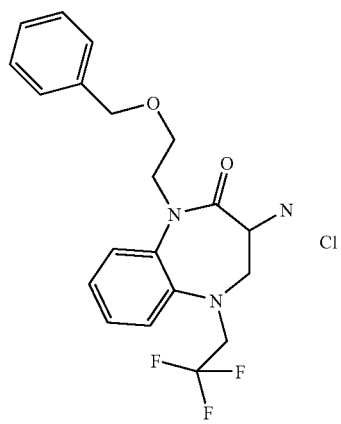

In an analogous manner to that described in Example 1d), the treatment of the [1-(2-benzyloxy-ethyl)-2-oxo-5-(2,2,2-trifluoro-ethyl)-2,3,4,5-tetrahydro-1H-benzo[b][1,4]diazepin-3-yl]-carbamic acid tert-butyl ester with hydrochlorid acid (37%) in dioxane yielded quantitatively the title compound as a light yellow solid; MS (m/e): 394 (M+H)$^+$.

c) N-[1-(2-Benzyloxy-ethyl)-2-oxo-5-(2,2,2-trifluoro-ethyl)-2,3,4,5-tetrahydro-1H-benzo[b][1,4]diazepin-3-yl]-2-hydroxy-2-methyl-N'-(2,2,3,3,3-pentafluoro-propyl)-malonamide (diast. racemate)

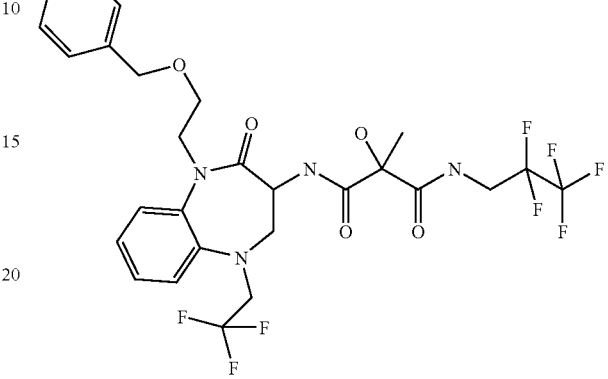

In an analogous manner to that described in Example 1e), the condensation of 3-amino-1-(2-benzyloxy-ethyl)-5-(2,2,2-trifluoro-ethyl)-1,3,4,5-tetrahydro-benzo[b][1,4]diazepin-2-one hydrochloride and (RS)-2-hydroxy-2-methyl-N-(2,2,3,3,3-pentafluoro-propyl)-malonamic acid with 1-hydroxy-benzotriazole and N-(3-dimethylaminpropyl)-N'-ethyl-carbodiimide hydrochloride as the condensating agents yielded a mixture of the four epimeric title compounds as a white foam; MS (m/e): 641 (M+H)$^+$.

The four epimers were separated by HPLC on a chiral phase (Chiralpak AD) using a 80:20-mixture of heptane and isopropanol as the eluent and were obtained in the following order:

(R or S)-(−)-N-[(S)-1-(2-benzyloxy-ethyl)-2-oxo-5-(2,2,2-trifluoro-ethyl)-2,3,4,5-tetrahydro-1H-benzo[b][1,4]diazepin-3-yl]-2-hydroxy-2-methyl-N'-(2,2,3,3,3-pentafluoro-propyl)-malonamide; [>99.5% d.e.; MS (m/e): 641 (M+H)$^+$];

(R or S)-(+)-N-[(R)-1-(2-benzyloxy-ethyl)-2-oxo-5-(2,2,2-trifluoro-ethyl)-2,3,4,5-tetrahydro-1H-benzo[b][1,4]diazepin-3-yl]-2-hydroxy-2-methyl-N'-(2,2,3,3,3-pentafluoro-propyl)-malonamide [99.3% d.e.; MS (m/e): 641 (M+H)$^+$];

(S or R)-(+)-N-[(R)-1-(2-benzyloxy-ethyl)-2-oxo-5-(2,2,2-trifluoro-ethyl)-2,3,4,5-tetrahydro-1H-benzo[b][1,4]diazepin-3-yl]-2-hydroxy-2-methyl-N'-(2,2,3,3,3-pentafluoro-propyl)-malonamide [87.2% d.e.; MS (m/e): 641 (M+H)$^+$];

(S or R)-(−)-N-[(S)-1-(2-benzyloxy-ethyl)-2-oxo-5-(2,2,2-trifluoro-ethyl)-2,3,4,5-tetrahydro-1H-benzo[b][1,4]diazepin-3-yl]-2-hydroxy-2-methyl-N'-(2,2,3,3,3-pentafluoro-propyl)-malonamide; [>99.5% d.e.; MS (m/e): 641 (M+H)$^+$] as a white foam each.

d) (R or S)-2-Hydroxy-N-[(S)-1-(2-hydroxy-ethyl)-2-oxo-5-(2,2,2-trifluoro-ethyl)-2,3,4,5-tetrahydro-1H-benzo[b][1,4]diazepin-3-yl]-2-methyl-N'-(2,2,3,3,3-pentafluoro-propyl)-malonamide In an analogous procedure to that described in Example 8d), the hydrogenolysis of the first eluting epimer (R or S)-

(−)-N-[(S)-1-(2-benzyloxy-ethyl)-2-oxo-5-(2,2,2-trifluoro-ethyl)-2,3,4,5-tetrahydro-1H-benzo[b][1,4]diazepin-3-yl]-2-hydroxy-2-methyl-N'-(2,2,3,3,3-pentafluoro-propyl)-malonamide using palladium on carbon (10%) as the catalyst yielded the title compound as a white foam (yield 75% of theory); MS (m/e): 551 (M+H)⁺.

EXAMPLE 10

(S)-3-[(R or S)-2-Hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester and (S)-3-[(S or R)-2-Hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester

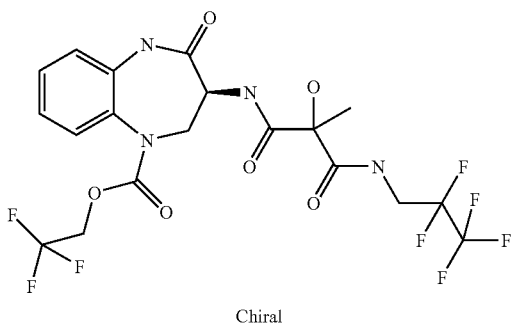

Chiral a) (S)-3-tert-Butoxycarbonylamino-4-oxo-2,3,4,5-tetrahydro-benzo[b][1,4]diazepine-1-carboxylic acid 2,2,2-trifluoro-ethyl ester and (S)-3-tert-Butoxycarbonylamino-4-oxo-5-(2,2,2-trifluoro-ethyl)-2,3,4,5-tetrahydro-benzo[b][1,4]diazepine-1-carboxylic acid 2,2,2-trifluoro-ethyl ester

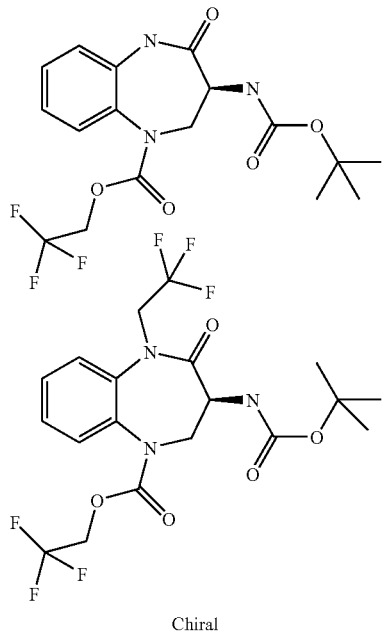

Chiral

In an analogous manner to that described in Example 1c), the (S)-2-oxo-2,3,4,5-tetrahydro-1H-benzo[b][1,4]diazepin-3-yl)-carbamic acid tert-butyl ester was treated with 2,2,2-trifluoroethyl trifluoromethanesulphonate, cesium carbonate, and solid carbondioxide in DMF to yield after chromatography the (S)-3-tert-butoxycarbonylamino-4-oxo-2,3,4,5-tetrahydro-benzo[b][1,4]diazepine-1-carboxylic acid 2,2,2-trifluoro-ethyl ester as a white foam [yield 68% of theory; MS (m/e): 404 (M+H)⁺] and the (S)-3-tert-butoxycarbonylamino-4-oxo-5-(2,2,2-trifluoro-ethyl)-2,3,4,5-tetrahydro-benzo[b][1,4]diazepine-1-carboxylic acid 2,2,2-trifluoro-ethyl ester as a white solid [yield 18% of theory; MS (m/e): 486 (M+H)⁺].

b) (S)-3-Amino-4-oxo-2,3,4,5-tetrahydro-benzo[b][1,4]diazepine-1-carboxylic acid 2,2,2-trifluoro-ethyl ester Hydrochloride

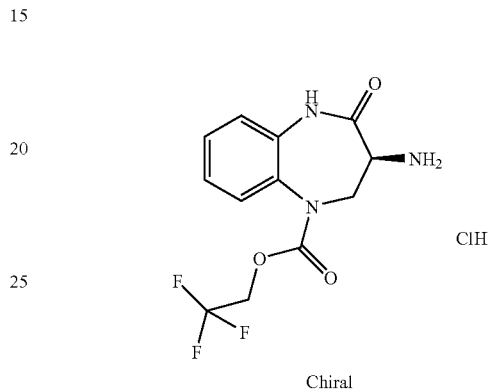

Chiral

In an analogous manner to that described in Example 1d), the treatment of the (S)-3-tert-butoxycarbonylamino-4-oxo-2,3,4,5-tetrahydro-benzo[b][1,4]diazepine-1-carboxylic acid 2,2,2-trifluoro-ethyl ester with hydrochlorid acid (37%) in dioxane yielded (98% of theory) the title compound as an off-white solid; MS (m/e): 304 (M+H)⁺.

c) (S)-3-[(R or S)-2-Hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester and (S)-3-[(S or R)-2-Hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester In an analogous manner to that described in Example 1e), the condensation of (S)-3-amino-4-oxo-2,3,4,5-tetrahydro-benzo[b][1,4]diazepine-1-carboxylic acid 2,2,2-trifluoro-ethyl ester hydrochloride and (RS)-2-hydroxy-2-methyl-N-(2,2,3,3,3-pentafluoro-propyl)-malonamic acid with 1-hydroxy-benzotriazole and N-(3-dimethylaminpropyl)-N'-ethyl-carbodiimide hydrochloride as the condensating agents yielded a 1:1-mixture of the epimeric title compounds as a white foam; MS (m/e): 551 (M+H)⁺.

The two epimers were separated by HPLC on a chiral phase (Chiralpak AD) using a 85:15-mixture of heptane and ethanol as the eluent yielding the first eluting epimer (S)-3-[(R or S)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester as a yellow foam [MS (m/e): 551 (M+H)⁺] and the second eluting epimer (S)-3-[(S or R)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester as a white foam [MS (m/e) 551 (M+H)⁺].

EXAMPLE 11

(S)-3-[(R or S)-2-Hydroxy-2-(2,2,3,3,3-pentafluoro-propylcarbamoyl)-propionylamino]-4-oxo-5-(2,2,2-trifluoro-ethyl)-2,3,4,5-tetrahydro-benzo[b][1,4]diazepine-1-carboxylic acid 2,2,2-trifluoro-ethyl ester and (S)-3-[(S or R)-2-Hydroxy-2-(2,2,3,3,3-pentafluoro-propylcarbamoyl)-propionylamino]-4-oxo-5-(2,2,2-trifluoro-ethyl)-2,3,4,5-tetrahydro-benzo[b][1,4]diazepine-1-carboxylic acid 2,2,2-trifluoro-ethyl ester

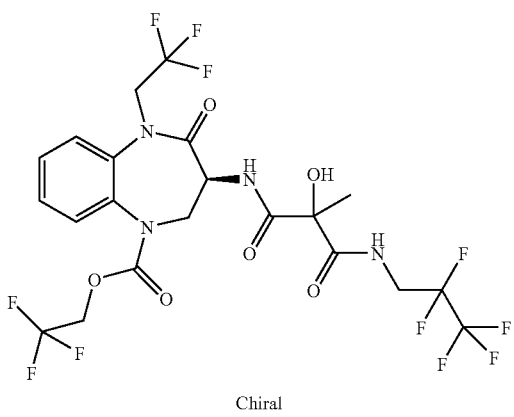

Chiral a) (S)-3-Amino-4-oxo-5-(2,2,2-trifluoro-ethyl)-2,3,4,5-tetrahydro-benzo[b][1,4]diazepine-1-carboxylic acid 2,2,2-trifluoro-ethyl ester Hydrochloride

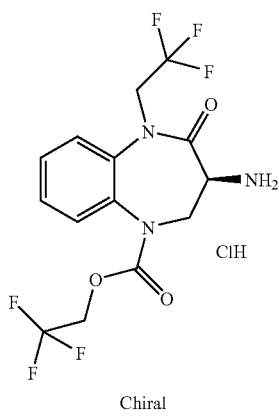

Chiral

In an analogous manner to that described in Example 1d), the treatment of the (S)-3-tert-butoxycarbonylamino-4-oxo-5-(2,2,2-trifluoro-ethyl)-2,3,4,5-tetrahydro-benzo[b][1,4]diazepine-1-carboxylic acid 2,2,2-trifluoro-ethyl ester [Example 10a)] with hydrochlorid acid (37%) in dioxane yielded (93% of theory) the title compound as a light yellow solid; MS (m/e): 386 (M+H)$^+$.

b) (S)-3-[(R or S)-2-Hydroxy-2-(2,2,3,3,3-pentafluoro-propylcarbamoyl)-propionylamino]-4-oxo-5-(2,2,2-trifluoro-ethyl)-2,3,4,5-tetrahydro-benzo[b][1,4]diazepine-1-carboxylic acid 2,2,2-trifluoro-ethyl ester and (S)-3-[(S or R)-2-Hydroxy-2-(2,2,3,3,3-pentafluoro-propylcarbamoyl)-propionylamino]-4-oxo-5-(2,2,2-trifluoro-ethyl)-2,3,4,5-tetrahydro-benzo[b][1,4]diazepine-1-carboxylic acid 2,2,2-trifluoro-ethyl ester In an analogous manner to that described in Example 1e), the condensation of (S)-3-amino-4-oxo-5-(2,2,2-trifluoro-ethyl)-2,3,4,5-tetrahydro-benzo[b][1,4]diazepine-1-carboxylic acid 2,2,2-trifluoro-ethyl ester hydrochloride and (RS)-2-hydroxy-2-methyl-N-(2,2,3,3,3-pentafluoro-propyl)-malonamic acid with 1-hydroxy-benzotriazole and N-(3-dimethylaminpropyl)-N'-ethyl-carbodiimide hydrochloride as the condensating agents yielded a 1:1-mixture of the epimeric title compounds as a white foam; MS (m/e) 633 (M+H)$^+$.

The two epimers were separated by HPLC on a chiral phase (Chiralcel OD) using a 90:10-mixture of heptane and isopropanol as the eluent yielding the first eluting epimer (S)-3-[(R or S)-2-hydroxy-2-(2,2,3,3,3-pentafluoro-propylcarbamoyl)-propionylamino]-4-oxo-5-(2,2,2-trifluoro-ethyl)-2,3,4,5-tetrahydro-benzo[b][1,4]diazepine-1-carboxylic acid 2,2,2-trifluoro-ethyl ester as a light yellow foam [MS (m/e): 633 (M+H)$^+$] and the second eluting epimer (S)-3-[(S or R)-2-hydroxy-2-(2,2,3,3,3-pentafluoro-propylcarbamoyl)-propionylamino]-4-oxo-5-(2,2,2-trifluoro-ethyl)-2,3,4,5-tetrahydro-benzo[b][1,4]diazepine-1-carboxylic acid 2,2,2-trifluoro-ethyl ester as a white foam [MS (m/e): 633 (M+H)$^+$].

EXAMPLE 12

(S)-5-(2-Hydroxy-ethyl)-3-[(S or R)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester

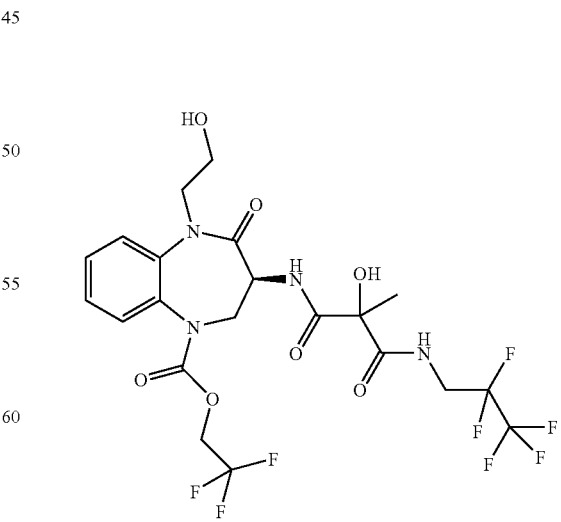

Chiral a) [(S)-1-(2-Benzyloxy-ethyl)-2-oxo-2,3,4,5-tetrahydro-1H-benzo[b][1,4]diazepin-3-yl]-carbamic acid tert-butyl ester

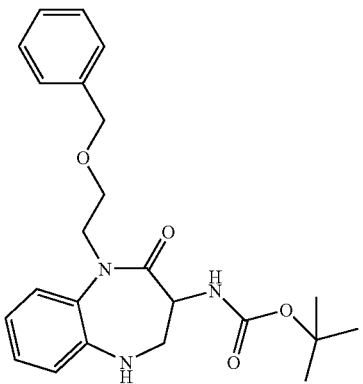

A solution of 2.0 g of (S)-2-oxo-2,3,4,5-tetrahydro-1H-benzo[b][1,4]diazepin-3-yl)-carbamic acid tert-butyl ester in 70 ml of tetrahydrofurane was cooled to −78° C. under an inert atmosphere and treated with 10.1 ml of a 1M solution of lithium bis(trimethylsilyl)amide in tetrahydrofurane. Stirring at −78° C. was continued for 30 minutes before the reaction mixture was warmed to room temperature. After the addition of 2.24 ml of benzyl 2-bromoethylether and 1.38 g of lithium iodide, the reaction mixture was stirred at room temperature for 5 days. For the working-up, the reaction mixture was evaporated under reduced pressure and the residue was directly submitted to purification by chromatography on a Si—NH$_2$ phase (ISOLUTE®) using a gradient of heptane/ethyl acetate=100/0 to 50/50 as the eluent. There were obtained 0.716 g (24% of theory) of the title compound as a white foam; MS (m/e): 412 (M+H)$^+$.

b) (S)-5-(2-Benzyloxy-ethyl)-3-tert-butoxycarbonylamino-4-oxo-2,3,4,5-tetrahydro-benzo[b][1,4]diazepine-1-carboxylic acid 2,2,2-trifluoro-ethyl ester

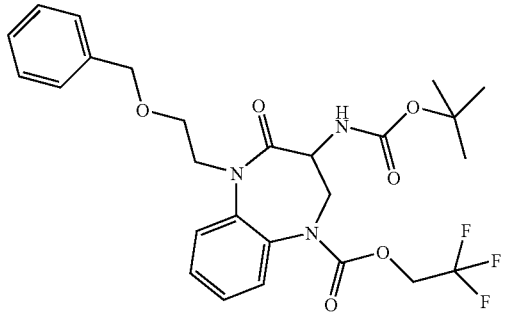

A solution of 301 mg of [(RS)-1-(2-benzyloxy-ethyl)-2-oxo-2,3,4,5-tetrahydro-1H-benzo[b][1,4]diazepin-3-yl]-carbamic acid tert-butyl ester in 6 ml of N,N-dimethylformamide was treated with 477 mg of cesium carbonate, 350 mg of 2,2,2-trifluoroethyl trifluoromethanesulphonate, and about 300 mg of solid carbondioxide. The reaction mixture was stirred in a sealed tube at 60° C. for 18 hours. For the working-up, the solvent was evaporated under reduced pressure, and the residue was distributed between 10 ml of a saturated sodium hydrogencarbonate solution and 30 ml of ethyl acetate. The aqueous layer was separated and extracted twice with 30 ml of ethyl acetate. The combined organic layers were dried over sodium sulphate and evaporated under reduced pressure. For purification, the light brown oil was separated on silica gel using a gradient of heptane/ethyl acetate=100/0 to 60/20 as the eluent. There were obtained 325 mg (83% of theory) of the title compound as a white foam [MS (m/e): 538 (M+H)$^+$].

c) (S)-3-Amino-5-(2-benzyloxy-ethyl)-4-oxo-2,3,4,5-tetrahydro-benzo[b][1,4]diazepine-1-carboxylic acid 2,2,2-trifluoro-ethyl ester Hydrochloride

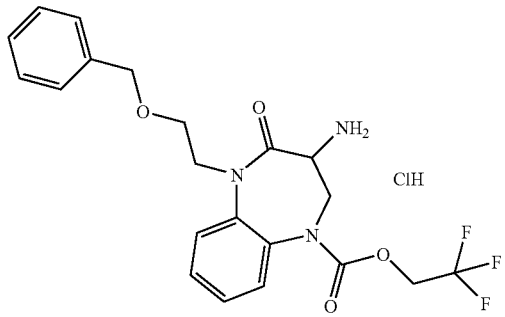

In an analogous manner to that described in Example 1d), the treatment of the (RS)-5-(2-benzyloxy-ethyl)-3-tert-butoxycarbonylamino-4-oxo-2,3,4,5-tetrahydro-benzo[b][1,4]diazepine-1-carboxylic acid 2,2,2-trifluoro-ethyl ester with hydrochlorid acid (37%) in dioxane yielded quantitatively the title compound as a light yellow foam; MS (m/e): 438 (M+H)$^+$.

d) (S)-5-(2-Benzyloxy-ethyl)-3-[(R or S)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester and (S)-5-(2-Benzyloxy-ethyl)-3-[(S or R)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester

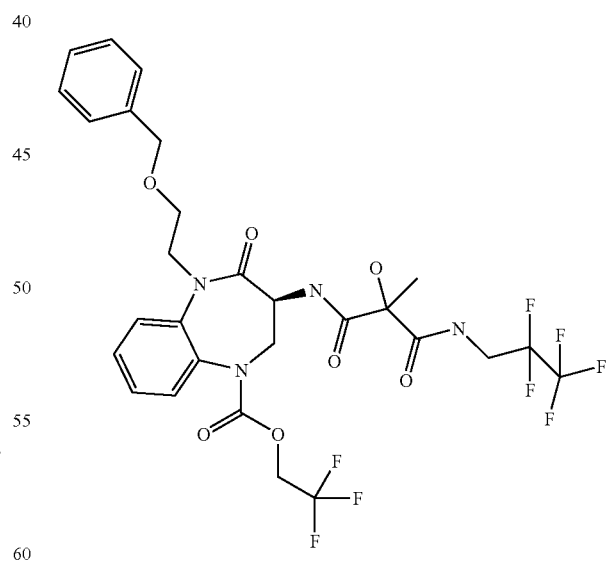

In an analogous manner to that described in Example 1e), the condensation of (S)-3-amino-5-(2-benzyloxy-ethyl)-4-oxo-2,3,4,5-tetrahydro-benzo[b][1,4]diazepine-1-carboxylic acid 2,2,2-trifluoro-ethyl ester hydrochloride and (RS)-2-hydroxy-2-methyl-N-(2,2,3,3,3-pentafluoro-propyl)-malonamic acid with 1-hydroxy-benzotriazole and N-(3- dimethylaminpropyl)-N'-ethyl-carbodiimide hydrochloride as the condensating agents yielded a 45.5:5.1:5.8:43.6-mixture of the partially epimerised title compounds as a white foam; MS (m/e): 685 (M+H)⁺.

The two major epimers were separated by HPLC on a chiral phase (Chiralcel OD) using a 95:5-mixture of heptane and ethanol as the eluent yielding the first eluting epimer (S)-5-(2-benzyloxy-ethyl)-3-[(R or S)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester [yield: 35% of theory; MS (m/e): 685 (M+H)⁺] and the last eluting epimer (S)-5-(2-benzyloxy-ethyl)-3-[(S or R)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester as a white foam [yield: 40% of theory; MS (m/e): 685 (M+H)⁺] both as an off-white foam.

e) (S)-5-(2-Hydroxy-ethyl)-3-[(S or R)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester In an analogous procedure to that described in Example 8d), the hydrogenolysis of the last eluting epimer (S)-5-(2-benzyloxy-ethyl)-3-[(S or R)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester using palladium on carbon (10%) as the catalyst yielded the title compound as a white foam (yield 79% of theory); MS (m/e): 595 (M+H)⁺.

EXAMPLE 13

(S)-3-[(R or S)-2-Hydroxy-2-(2,2,3,3,3-pentafluoro-propylcarbamoyl)-propionylamino]-4-oxo-5-(4,4,4-trifluoro-butyl)-2,3,4,5-tetrahydro-benzo[b][1,4]diazepine-1-carboxylic acid 4,4,4-trifluoro-butyl ester and (S)-3-[(S or R)-2-Hydroxy-2-(2,2,3,3,3-pentafluoro-propylcarbamoyl)-propionylamino]-4-oxo-5-(4,4,4-trifluoro-butyl)-2,3,4,5-tetrahydro-benzo[b][1,4]diazepine-1-carboxylic acid 4,4,4-trifluoro-butyl ester

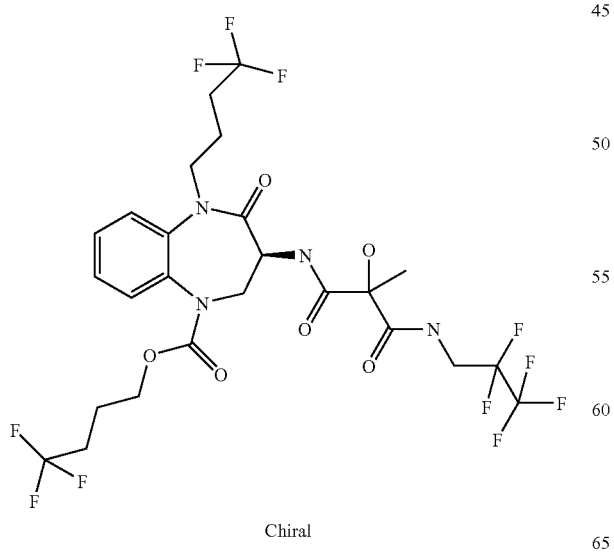

Chiral a) (S)-3-tert-Butoxycarbonylamino-4-oxo-5-(4,4,4-trifluoro-butyl)-2,3,4,5-tetrahydro-benzo[b][1,4]diazepine-1-carboxylic acid 4,4,4-trifluoro-butyl ester In an analogous manner to that described in Example 1c), the (S)-2-oxo-2,3,4,5-tetrahydro-1H-benzo[b][1,4]diazepin-3-yl)-carbamic acid tert-butyl ester was treated with 4-bromo-1,1,1-trifluoro-butane, lithium iodide, cesium carbonate, and solid carbondioxide in DMF to yield after chromatography the (S)-3-tert-butoxycarbonylamino-4-oxo-5-(4,4,4-trifluoro-butyl)-2,3,4,5-tetrahydro-benzo[b][1,4]diazepine-1-carboxylic acid 4,4,4-trifluoro-butyl ester as a white foam [yield 26% of theory; MS (m/e): 542 (M+H)⁺] and the [(S)-4-oxo-1-(4,4,4-trifluoro-butyl)-2,3,4,5-tetrahydro-1H-benzo[b][1,4]diazepin-3-yl]-carbamic acid tert-butyl ester [yield 17% of theory, MS (m/e): 388 (M+H)⁺].

b) (S)-3-Amino-4-oxo-5-(4,4,4-trifluoro-butyl)-2,3,4,5-tetrahydro-benzo[b][1,4]diazepine-1-carboxylic acid 4,4,4-trifluoro-butyl ester Hydrochloride

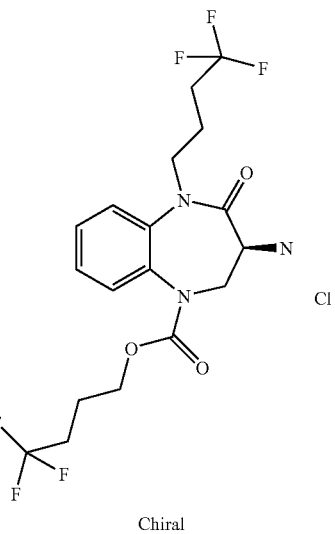

Chiral

In an analogous manner to that described in Example 1d), the treatment of the (S)-3-tert-butoxycarbonylamino-4-oxo-5-(4,4,4-trifluoro-butyl)-2,3,4,5-tetrahydro-benzo[b][1,4]diazepine-1-carboxylic acid 4,4,4-trifluoro-butyl ester with hydrochlorid acid (37%) in dioxane yielded quantitatively the title compound as a white foam; MS (m/e): 442 (M+H)⁺.

c) (S)-3-[(R or S)-2-Hydroxy-2-(2,2,3,3,3-pentafluoro-propylcarbamoyl)-propionylamino]-4-oxo-5-(4,4,4-trifluoro-butyl)-2,3,4,5-tetrahydro-benzo[b][1,4]diazepine-1-carboxylic acid 4,4,4-trifluoro-butyl ester and (S)-3-[(S or R)-2-Hydroxy-2-(2,2,3,3,3-pentafluoro-propylcarbamoyl)-propionylamino]-4-oxo-5-(4,4,4-trifluoro-butyl)-2,3,4,5-tetrahydro-benzo[b][1,4]diazepine-1-carboxylic acid 4,4,4-trifluoro-butyl ester In an analogous manner to that described in Example 1e), the condensation of (S)-3-amino-4-oxo-5-(4,4,4-trifluoro-butyl)-2,3,4,5-tetrahydro-benzo[b][1,4]diazepine-1-carboxylic acid 4,4,4-trifluoro-butyl ester hydrochloride and (RS)-2-hydroxy-2-methyl-N-(2,2,3,3,3-pentafluoro-propyl)-malonamic acid with 1-hydroxy-benzotriazole and N-(3-dimethylaminpropyl)-N'-ethyl-carbodiimide hydrochloride as the condensating agents yielded a 1:1-mixture of the title compounds as a white foam; MS (m/e): 689 (M+H)$^+$.

The two epimers were separated by HPLC on a chiral phase (Chiralpak AD) using a 70:30-mixture of heptane and isopropanol as the eluent yielding the first eluting epimer (S)-3-[(R or S)-2-hydroxy-2-(2,2,3,3,3-pentafluoro-propylcarbamoyl)-propionylamino]-4-oxo-5-(4,4,4-trifluoro-butyl)-2,3,4,5-tetrahydro-benzo[b][1,4]diazepine-1-carboxylic acid 4,4,4-trifluoro-butyl ester [yield: 42% of theory; MS (m/e): 689 (M+H)$^+$] and the second eluting epimer (S)-3-[(S or R)-2-hydroxy-2-(2,2,3,3,3-pentafluoro-propylcarbamoyl)-propionylamino]-4-oxo-5-(4,4,4-trifluoro-butyl)-2,3,4,5-tetrahydro-benzo[b][1,4]diazepine-1-carboxylic acid 4,4,4-trifluoro-butyl ester [yield: 42% of theory; MS (m/e): 689 (M+H)$^+$] both as a light yellow foam.

EXAMPLE 14

(S)-5-(2-Hydroxy-ethyl)-3-[(S or R)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2-hydroxy-ethyl ester

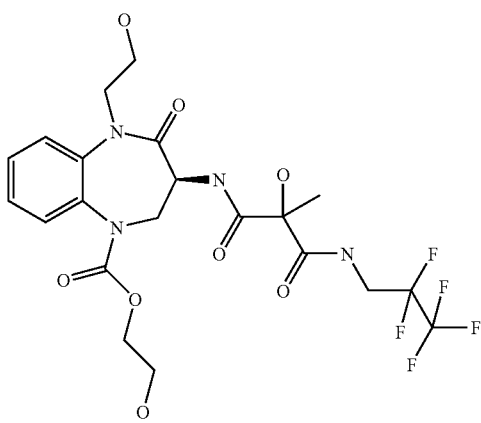

Chiral a) (S)-5-(2-Benzyloxy-ethyl)-3-tert-butoxycarbonylamino-4-oxo-2,3,4,5-tetrahydro-benzo[b][1,4]diazepine-1-carboxylic acid 2-benzyloxy-ethyl ester

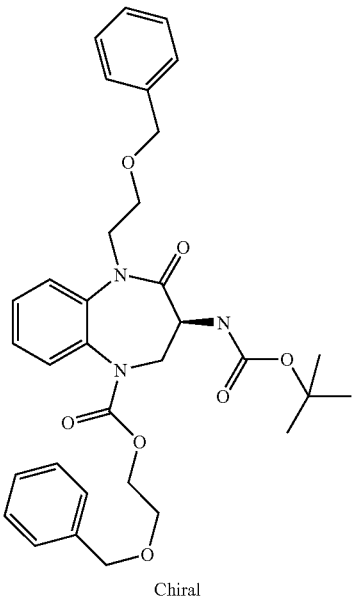

Chiral

In an analogous manner to that described in Example 1c), the (S)-2-oxo-2,3,4,5-tetrahydro-1H-benzo[b][1,4]diazepin-3-yl)-carbamic acid tert-butyl ester was treated with (2-bromo-ethoxymethyl)-benzene, lithium iodide, cesium carbonate, and solid carbondioxide in DMF to yield after chromatography the (S)-5-(2-benzyloxy-ethyl)-3-tert-butoxycarbonylamino-4-oxo-2,3,4,5-tetrahydro-benzo[b][1,4]diazepine-1-carboxylic acid 2-benzyloxy-ethyl as a colourless viscous oil [yield 31% of theory, MS (m/e): 590 (M+H)$^+$] and the (S)-3-tert-butoxycarbonylamino-4-oxo-2,3,4,5-tetrahydro-benzo[b][1,4]diazepine-1-carboxylic acid 2-benzyloxy-ethyl ester [yield 19% of theory, MS (m/e): 456 (M+H)$^+$] as a white foam.

b) (S)-3-Amino-5-(2-benzyloxy-ethyl)-4-oxo-2,3,4,5-tetrahydro-benzo[b][1,4]diazepine-1-carboxylic acid 2-benzyloxy-ethyl ester Hydrochloride

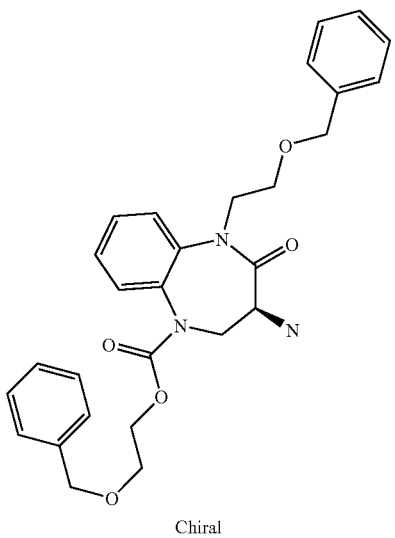

Chiral

In an analogous manner to that described in Example 1d), the treatment of the (S)-5-(2-benzyloxy-ethyl)-3-tert-butoxycarbonylamino-4-oxo-2,3,4,5-tetrahydro-benzo[b][1,4]diazepine-1-carboxylic acid 2-benzyloxy-ethyl ester with hydrochlorid acid (37%) in dioxane yielded quantitatively the title compound as a viscous light yellow oil; MS (m/e): 490 (M+H)$^+$.

c) (S)-5-(2-Benzyloxy-ethyl)-3-[(R or S)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2-benzyloxy-ethyl ester and (S)-5-(2-Benzyloxy-ethyl)-3-[(S or R)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2-benzyloxy-ethyl ester

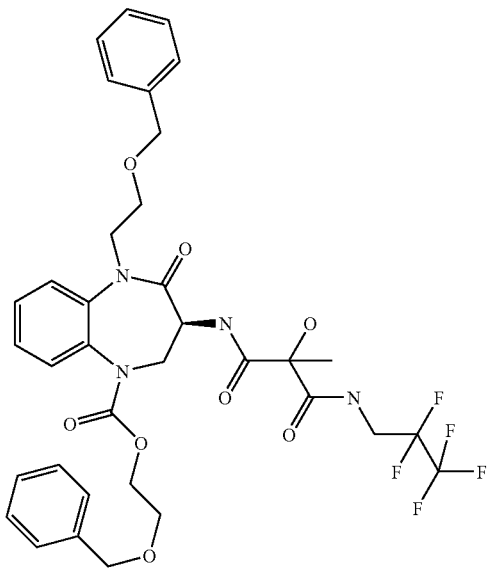

In an analogous manner to that described in Example 1e), the condensation of (S)-3-amino-5-(2-benzyloxy-ethyl)-4-oxo-2,3,4,5-tetrahydro-benzo[b][1,4]diazepine-1-carboxylic acid 2-benzyloxy-ethyl ester hydrochloride and (RS)-2-hydroxy-2-methyl-N-(2,2,3,3,3-pentafluoro-propyl)-malonamic acid with 1-hydroxy-benzotriazole and N-(3-dimethylaminpropyl)-N'-ethyl-carbodiimide hydrochloride as the condensating agents yielded a 1:1-mixture of the title compounds as a colourless viscous oil; MS (m/e): 737 (M+H)$^+$.

The two epimers were separated by HPLC on a chiral phase (Chiralpak AD) using a 80:20-mixture of heptane and ethanol as the eluent yielding the first eluting epimer (S)-5-(2-benzyloxy-ethyl)-3-[(R or S)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2-benzyloxy-ethyl ester [yield: 35% of theory; MS (m/e): 737 (M+H)$^+$] and the second eluting epimer (S)-5-(2-benzyloxy-ethyl)-3-[(S or R)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2-benzyloxy-ethyl ester [yield: 42% of theory; MS (m/e): 737 (M+H)$^+$] both as a white solid.

d) (S)-5-(2-Hydroxy-ethyl)-3-[(S or R)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2-hydroxy-ethyl ester In an analogous procedure to that described in Example 7d), the second eluting epimer (S)-5-(2-benzyloxy-ethyl)-3-[(S or R)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2-benzyloxy-ethyl ester was treated with palladium on carbon (10%) as the catalyst and stirred for 7 days under an atmosphere of hydrogen. During this period of time, the catalyst was replaced three times after filtration of the reaction mixture over Dicalit. The title compound was obtained as a white foam (yield 66% of theory); MS (m/e): 557 (M+H)$^+$.

The compounds of formula I and their pharmaceutically usable addition salts possess valuable pharmacological properties. Specifically, it has been found that the compounds of the present invention may inhibit the γ-secretase.

The compounds were investigated in accordance with the test given hereinafter.

Description of γ-Secretase Assay

The activity of test compounds can be evaluated in assays which measure the proteolytic cleavage of suitable substrates by γ-secretase activity. These can be cellular assays where e.g., a substrate of the γ-secretase is fused in its cytoplasmic domain to a transcription factor. Cells are transfected with this fusion gene and a reporter gene, e.g., firefly luciferase, which expression is enhanced by the transcription factor. Cleavage of the fused substrate by γ-secretase will lead to expression of the reporter gene which can be monitored in appropriate assays. The γ-secretase activity can also be determined in cell-free in vitro assays where e.g., a cell lysate containing the γ-secretase complex is incubated with a suitable APP-derived substrate which is cleaved to the Abeta peptides. The amount of produced peptides can be determined with specific ELISA assays. Cell lines of neuronal origin secrete Abeta peptides which can be measured with the specific ELISA assay. Treatment with compounds which inhibit γ-secretase leads to a reduction of secreted Abeta thus providing a measure of inhibition.

The in vitro assay of γ-secretase activity uses a HEK293 membrane fraction as a source of γ-secretase and a recombinant APP substrate. Latter consist of the C-terminal 100 amino acids of human APP fused to a 6×Histidin tail for purification which is expressed in E. coli in a regulatable expression vector, e.g. pEt15. This recombinant protein corresponds to the truncated APP fragment which results after γ-secretase cleavage of the extracellular domain and which constitutes the γ-secretase substrate. The assay principle is described in Li YM et al, PNAS 97(11), 6138-6143 (2000). Hek293 cells are mechanically disrupted and the microsomal fraction is isolated by differential centrifugation. The membranes are solubilized in detergent (0.25% CHAPSO) and incubated with the APP substrate. The Abeta peptides which are produced by γ-secretase cleavage of the substrate are detected by specific ELISA assays as described (Brockhaus M et al, Neuroreport 9(7), 1481-1486 (1998).

The preferred compounds show a IC$_{50}$<100 (nM). In the list below are described the data to the γ-secretase inhibition:

| Example No. | IC$_{50}$ in vitro (nM) |
|---|---|
| 1 | 81 |
| 2 | 14 |
| 3 | 8 |
| 4 | 16 |
| 5 | 2 |
| 6 | 2 |
| 7 | 29 |
| 8 | 24 |
| 9 | 6 |
| 10 | 6 |
| 11 | 9 |
| 12 | 11 |
| 13 | 15 |
| 14 | 16 |

In addition, the compounds of the present invention have been tested in a THESA assay for determination of the thermodynamic solubility.

THESA Assay:

Approximately 2 mg of each compound was added in excess to a 50 mM phosphate buffer, at room temperature (22.5±1° C.). Each sample was placed in a microanalysis tube, which was sonicated for 1 h and agitated for 2 h. All suspensions were left overnight. At the next day all pHs were measured with a pH-meter and the samples filtered with a micronic filterplate (MSGVN2250) to separate the solid material from the solution. Then, all solutions were analyzed by HPLC. The calibration line was established by different concentrations of the compound in DMSO. From this regression equation the solubility of the compound was determined.

| Example No. | THESA (µg/ml) |
|---|---|
| 1 | 77 |
| 5 | 67 |
| 6 | 124 |
| 8 | 2671 |
| 9 | 1781 |
| 10 | 74 |
| 12 | 3226 |
| 14 | 5184 |

The compounds of formula I of the present invention are further characterized by high metabolic stability. This parameter is a prerequisite for good bioavailability, which is necessary to obtain medicaments with acceptable in-vivo activity. The metabolic stability has been tested by the following method:

Microsome Incubation

Incubation mixtures consisted of liver microsomes (rat 1.0 mg prot/mL or human 2.0 mg prot/mL), test compound 10 µM, MgCl$_2$ (3.3 mM), and an NADPH regenerating system consisting of glucose-6-phosphate dehydrogenase, NADPH and glucose-6-phosphate (equivalent to 1 mM NADPH) in a total volume of 1.0 mL of potassium phosphate buffer 100 mM pH 7.4. Reactions were initiated by addition of the NADPH regenerating system at 37° C. At the time of 1, 5, 9, 13, 17, 21, 25, and 29 min a 5 µL aliquot was directly analysed on a HPLC-MS/MS system consisting of a HP 1100 quaternary pump with degasser and a PE-Sciex API-2000 MS/MS spectrometer. The analytical column was a Waters Symmetry Shield RP8 (2.1*50 mm with a 3.5 µM particle size). A polarity non linear gradient from phase A (MeOH/Ac. Form. 1% 20/80) to phase B (MeOH) was applied for a total run time of 2 minutes at a flow rate of 0.25 mL/min. The PE-Sciex API-2000 MS/MS spectrometer was used for detection of the parent compound. In vivo metabolic clearance was predicted according to published procedures [Houston, Biochem. Pharmacol. 47:1469-1479 (1994)]. In brief, the intrinsic clearance (Clearance, see table below) is calculated from the measured in vitro half-life taking into account incubation volume and microsomal protein used for the in vitro incubation. The intrinsic clearance is expressed in terms of µl/min/mg microsomal protein. For in vivo extrapolations, the hepatic extraction ratio (E) was calculated. Here it is reported the % MAB value which is equal to 1-E. The MAB (maximal achievable bioavailability) values express the maximal bioavailability that one can achieve with the given clearance values.

| Ex. | Intrinsic clearance (mouse) (µl/min/mg) | MAB (mouse) | Intrinsic clearance (human) (µl/min/mg) | MAB (human) |
|---|---|---|---|---|
| 1 | 22.4 | 58.5% | 0.05 | 99.7% |
| 2 | 6.5 | 83.0% | 13.1 | 54.3% |
| 3 | 125.7 | 20.1% | 11.9 | 56.7% |
| 4 | 129.6 | 19.6% | 12.5 | 55.5% |
| 5 | 261.6 | 10.8% | 18.6 | 45.5% |
| 6 | 94.9 | 25.0% | 15.9 | 49.4% |
| 7 | 32.5 | 49.3% | 5.2 | 74.9% |
| 8 | 52.7 | 37.5% | 0 | 100.0% |
| 9 | 65.2 | 32.7% | 2.1 | 88.2% |
| 10 | 5.4 | 85.5% | 0 | 100.0% |
| 11 | 10.6 | 74.9% | 0 | 100.0% |
| 12 | 0.9 | 97.2% | 2.9 | 84.3% |
| 13 | 0 | 100 | 2.2 | 87.4% |
| 14 | 12.3 | 72.1% | 13.6 | 53.3% |

The advantage of compounds disclosed by formula I of the present invention is their very good activity for γ-secretase inhibition, a good in vivo activity, a good thermodynamic solubility and bioavailability if compounds with similar structures or structures known in the art (WO 2005/023772), as shown in the table below:

| Structure | Cell-free IC$_{50}$ (nM) | THESA (μg/ml) | MAB (mouse) | MAB (human) |
|---|---|---|---|---|
| 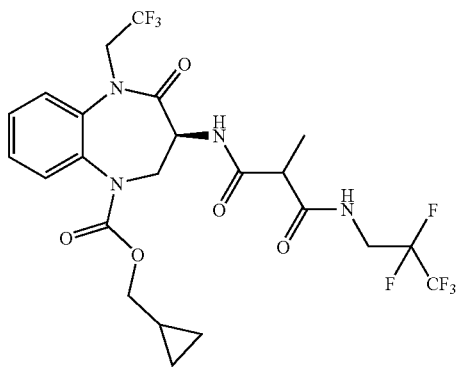  Example 109 of WO 2005/023772 | 48 | n.t. | 47.6% | 26.8% |
| 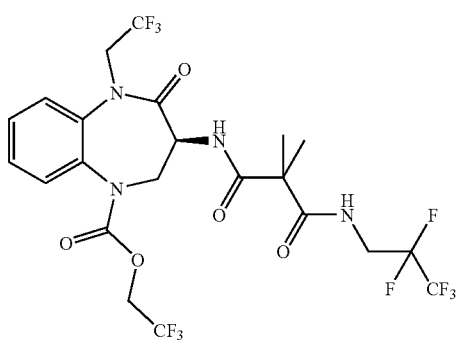  structure-related compound to Example 11 | 37 | 16 | 28.4% | 19.6% |
| 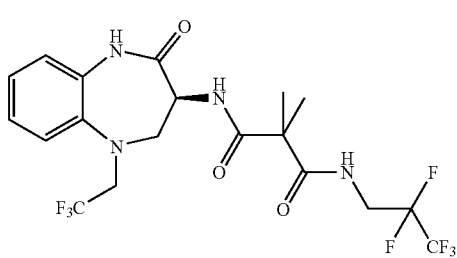  structure-related compound to Example 4 | 114 | <1 | 21.8% | 43.1% |
| 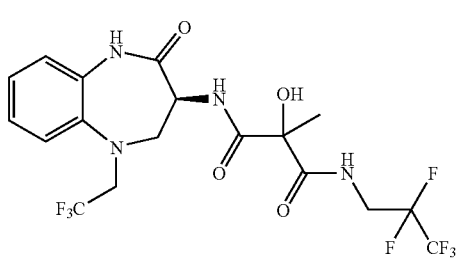  Example 4 of the present invention | 16 | n.t. | 19.6% | 55.5% |

-continued

| Structure | Cell-free IC$_{50}$ (nM) | THESA (µg/ml) | MAB (mouse) | MAB (human) |
|---|---|---|---|---|
| Example 11 of the present invention | 9 | 37 | 74.9% | 100.0% |

The present invention also provides pharmaceutical compositions containing compounds of the invention, for example compounds of formula I, and their pharmaceutically acceptable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the inhibition of the γ-secretase, such as of Alzheimer's disease. The invention also provides a method for treating Alzheimer's disease which comprises administering to an individual a therapeutically effective amount of a compound of formula I or a pharmaceutically acceptable salt thereof.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| | | Tablet Formulation (Wet Granulation) mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| | | Capsule Formulation mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |

-continued

| | | Capsule Formulation mg/capsule | | | |
|---|---|---|---|---|---|
| Item | Ingredients | 5 mg | 25 mg | 100 mg | 500 mg |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:
1. A compound of formula I

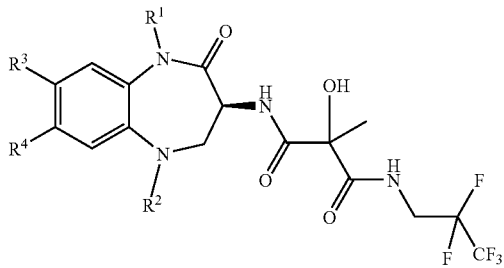

wherein
$R^1$ is hydrogen, lower alkyl substituted by halogen or lower alkyl substituted by hydroxy;
$R^2$ is lower alkyl substituted by halogen or lower alkyl substituted by hydroxy, or is —COO(CH$_2$)$_n$R$^5$;
n is 1, 2, or 3;
$R^5$ is hydroxy for n=2 or 3 or is lower alkyl substituted by halogen for n=1, 2 or 3; and
$R^3$ and $R^4$ are each independently hydrogen or halogen;
or a pharmaceutically suitable acid addition salt, optically pure enantiomer, racemate or diastereomeric mixture thereof.

2. The compound of claim 1, wherein $R^2$ is lower alkyl substituted by halogen.

3. The compound of claim 2, selected from the group consisting of
N-[(S)-7-Fluoro-4-oxo-1-(2,2,2-trifluoro-ethyl)-2,3,4,5-tetrahydro-1H-benzo[b][1,4]diazepin-3-yl]-(R or S)-2-hydroxy-2-methyl-N'-(2,2,3,3,3-pentafluoro-propyl)-malonamide,
(R or S)-2-Hydroxy-2-methyl-N-[(S)-4-oxo-1-(2,2,2-trifluoro-ethyl)-2,3,4,5-tetrahydro-1H-benzo[b][1,4]diazepin-3-yl]-N'-(2,2,3,3,3-pentafluoro-propyl)-malonamide,
(S or R)-2-Hydroxy-2-methyl-N-[(S)-4-oxo-1-(3,3,3-trifluoro-propyl)-2,3,4,5-tetrahydro-1H-benzo[b][1,4]diazepin-3-yl]-N'-(2,2,3,3,3-pentafluoro-propyl)-malonamide,
(R or S)-2-Hydroxy-2-methyl-N-[(S)-4-oxo-1-(4,4,4-trifluoro-butyl)-2,3,4,5-tetrahydro-1H-benzo[b][1,4]diazepin-3-yl]-N'-(2,2,3,3,3-pentafluoro-propyl)-malonamide, and
(R or S)-2-Hydroxy-N-[(S)-1-(2-hydroxy-ethyl)-2-oxo-5-(2,2,2-trifluoro-ethyl)-2,3,4,5-tetrahydro-1H-benzo[b][1,4]diazepin-3-yl]-2-methyl-N'-(2,2,3,3,3-pentafluoro-propyl)-malonamide.

4. The compound of claim 1, wherein $R^2$ is lower alkyl substituted by hydroxy.

5. The compound of claim 4, selected from the group consisting of
(RS)-2-Hydroxy-N-[(S)-1-(2-hydroxy-ethyl)-4-oxo-2,3,4,5-tetrahydro-1H-benzo[b][1,4]diazepin-3-yl]-2-methyl-N'-(2,2,3,3,3-pentafluoro-propyl)-malonamide and
(R or S)-2-Hydroxy-N-[(S)-5-(2-hydroxy-ethyl)-2-oxo-1-(2,2,2-trifluoro-ethyl)-2,3,4,5-tetrahydro-1H-benzo[b][1,4]diazepin-3-yl]-2-methyl-N'-(2,2,3,3,3-pentafluoro-propyl)-malonamide.

6. The compound of claim 1, wherein $R^2$ is —C(OO(CH$_2$)$_n$R$^5$, n is 1, 2, or 3, and $R^5$ is hydroxy for n=2 or 3, or is lower alkyl substituted by halogen for n=1, 2 or 3.

7. The compound of claim 6, selected from the group consisting of
(S)-7,8-Difluoro-3-[(R or S)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester,
(S)-7,8-Difluoro-3-[(S or R)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester,
(S)-7,8-Difluoro-3-[(R or S)-2-hydroxy-2-(2,2,3,3,3-pentafluoro-propylcarbamoyl)-propionylamino]-4-oxo-5-(2,2,2-trifluoro-ethyl)-2,3,4,5-tetrahydro-benzo[b][1,4]diazepine-1-carboxylic acid 2,2,2-trifluoro-ethyl ester,
(S)-3-[(R or S)-2-Hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester,
(S)-3-[(S or R)-2-Hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester,
(S)-3-[(S or R)-2-Hydroxy-2-(2,2,3,3,3-pentafluoro-propylcarbamoyl)-propionylamino]-4-oxo-5-(2,2,2-trifluoro-ethyl)-2,3,4,5-tetrahydro-benzo[b][1,4]diazepine-1-carboxylic acid 2,2,2-trifluoro-ethyl ester,
(S)-5-(2-Hydroxy-ethyl)-3-[(S or R)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2,2,2-trifluoro-ethyl ester,
(S)-3-[(S or R)-2-Hydroxy-2-(2,2,3,3,3-pentafluoro-propylcarbamoyl)-propionylamino]-4-oxo-5-(4,4,4-trifluoro-butyl)-2,3,4,5-tetrahydro-benzo[b][1,4]diazepine-1-carboxylic acid 4,4,4-trifluoro-butyl ester and
(S)-5-(2-Hydroxy-ethyl)-3-[(S or R)-2-hydroxy-2-(2,2,3,3,3-pentafluoro-propylcarbamoyl)-propionylamino]-4-oxo-2,3,4,5-tetrahydro-benzo[b][1,4]diazepine-1-carboxylic acid 2-hydroxy-ethyl ester.

8. A pharmaceutical composition comprising a compound of formula I

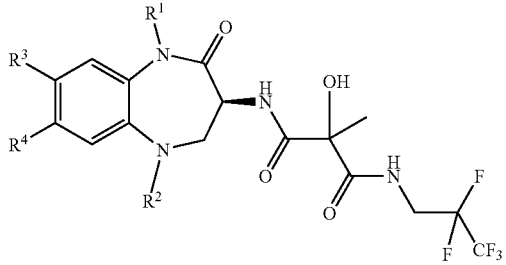

wherein $R^1$ is hydrogen, lower alkyl substituted by halogen or lower alkyl substituted by hydroxy;

$R^2$ is lower alkyl substituted by halogen or lower alkyl substituted by hydroxy, or is —COO(CH$_2$)$_n$R$^5$;

n is 1, 2, or 3;

$R^5$ is hydroxy for n=2 or 3 or is lower alkyl substituted by halogen for n=1, 2 or 3; and $R^3$ and $R^4$ are each independently hydrogen or halogen;

or a pharmaceutically suitable acid addition salt, optically pure enantiomer, racemate or diastereomeric mixture thereof and a pharmaceutically acceptable carrier.

* * * * *